(12) United States Patent
Yeh et al.

(10) Patent No.: US 8,507,506 B2
(45) Date of Patent: Aug. 13, 2013

(54) THEOPHYLLINE DERIVATIVE INHIBITS OSTEOPOROSIS

(75) Inventors: Jwu-Lai Yeh, Kaohsiung (TW); Ing-Jun Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 2 days.

(21) Appl. No.: 13/179,111

(22) Filed: Jul. 8, 2011

(65) Prior Publication Data
US 2012/0184570 A1 Jul. 19, 2012

(30) Foreign Application Priority Data
Jan. 14, 2011 (TW) .............................. 100101526 A

(51) Int. Cl.
*A61K 31/522* (2006.01)
(52) U.S. Cl.
USPC .................................................... 514/263.34
(58) Field of Classification Search
USPC .................................................... 514/263.34
See application file for complete search history.

(56) References Cited

U.S. PATENT DOCUMENTS
6,962,915 B2 * 11/2005 Das et al. .................. 514/234.2
2008/0312249 A1 12/2008 Chen

FOREIGN PATENT DOCUMENTS
TW 200848044 A 12/2008

OTHER PUBLICATIONS

Hirayama et al. (rheumatology (2002); 41:1232-1239).*
Armstrong et al., "A RANK/TRAF6-dependent Signal Transduction Pathway Is Essential for Osteoclast Cytoskeletal Organization and Resorptive Function," J. Biol. Chem. (2002) 277(46):44347-44356.
Mizukama et al., "Receptor Activator of NF-kB Ligand (RANKL) Activates TAK1 Mitogen-Activated Protein Kinase Kinase Kinase through a signaling complex containing RANK, TAB2, and TRAF6," Molecular and Cellular Biology (2002) 22(4):992-1000.
Miyamoto et al., "Reduction of bone Loss by Denbufylline, an Inhibitor of Phosphodiesterase 4," Biochemical Pharmacology (1997) 54(5):613-617.
Takayanagi, H., "The Role of NFAT in Osteoclast Formation," Ann NY Acad. Sci. (2007) 1116:227-237.
Wei et al., "Mechanisms modulating inflammatory osteolysis: A review with insights into therapeutic targets," Pathology Research and Practice (2008) 204(10):695-706.
Wong et al., "TRANCE, a TNF Family member, Activates Akt/PKB through a Signaling Complex Involving TRAF6 and c-Src," Molecular Cell (1999) 4(6):1041-1049.
Yoshimura et al., "Effects of cAMP-Phosphodiesterase Isozyme Inhibitor on Cytokine Production by Lipopolysaccharide-Stimulated Human Peripheral Blood Mononuclear Cells," Gen. Pharmac. (1997) 29(4):633-638.
Zhou et al., "HMGB1 Regulates RANKL-Induced Osteoclastogenesis in a Manner Dependent on RAGE," Journal of Bone and Mineral Research (2008) 23(7):1084-1096.
Hsu, Pei-Chuan, "Study the mechanism of KMUP-1 in attenuating RANKL-induced osteoclast-like cells proliferation and differentiation," A master thesis of Gratuate Institute of Pharmacology, Kaohsiung medical University, Taiwan (Published on Jul. 16, 2010).
Office Action, Taiwanese Patent Application No. 100101526, dated Feb. 8, 2013.

* cited by examiner

*Primary Examiner* — Shirley V Gembeh
(74) *Attorney, Agent, or Firm* — Volpe and Koenig, P.C.

(57) ABSTRACT

The theophylline derivative disclosed in the present invention is characterized by having the pharmaceutical functions of osteoporosis. The theophylline derivative protects against bone resorption and inflammatory mediator infiltration.

5 Claims, 20 Drawing Sheets

THEOPHYLLINE DERIVATIVE INHIBITS OSTEOPOROSIS

FIELD OF THE INVENTION

The present invention relates to applying theophylline derivative on treating osteoporosis. In particular, the medical compound including theophylline derivative can prevent and treat the processes of osteoporosis and reduces inflammatory mediator infiltration.

BACKGROUND OF THE INVENTION

Osteoporosis is a disease that disorder of osteoclasts and osteoblasts results in reducing bone densities and changing bone structures and further results in increasing the ratio of fracture. Osteoporosis companying with occurring of fracture does not only cause pain to human bodies but also increases patients' death ratio and serious economic burdens.

Osteoblasts, adipocytes, and fibroblasts are all divided from mesenchymal stem cells. However, osteoclasts are divided from macrophage/monocyte linage of hematopoietic cells. The two cytokinins, macrophage colony-stimulating factor, M-CSF, and receptor activator of nuclear factor-κB ligand, RANKL, which are secreted by bone marrow stromal cells and Osteoblasts and belong to tumor necrosis factor, TNF, are the essential factors for monocytic progenitor cells dividing to osteoclasts. RANKL is expressed on the surfaces of osteoblasts, bone marrow stromal cells and vascular endothelial cells. Moreover, RANKL can combine with RANK of monocytic progenitor cells' surface and stimulate cells to divide into coenocytic osteoclasts. At this time, maturely-divided osteoclasts secrete tartrate-resistant acid phosphatase, TRAP, to perform an ability of dissolving bones.

RANKL/RANK

RANK, the receptor of RANKL, is usually expressed on the cell membranes of progenitor cells of osteoclasts and maturely-divided osteoclasts. RANKL directly interacts with RANK by contact between cells, and stimulates osteoclasts to differentiate and proliferate to perform an ability of dissolving bones. After RANKL combines with RANK, RANK will interact with tumor necrosis factor receptor-associated factor, TRAFs, and switches on series signal transduction pathways of differentiation and activation of osteoclasts which include three major signal transduction pathways: (1) nuclear factor Kappa B, NF-κB, (2) mitogen activated protein kinase, MAP kinase or MAPK, and (3) Src/PI3K/Akt signal transduction pathways and important transcription factors, c-Fos and NFATc 1. NF-κB and MAP kinase signal transduction pathways regulate the ability of differentiation and dissolution of the osteoclasts. Also Wong, B R. etc. 1999, Mol. Cell. Vol. 4(6) 1041-1049 hold that Src/PI3K/Akt signal transduction pathway is the pathway that dominates survival of osteoclasts.

TRAFs

TRAF family includes six different proteins which can interact with RANK. Misukami, J. etc. 2002. Mol. Cell. Biol. Vol. 22(4) 992-1000 discovered that the mice only knocked down TRAF6 gene would have osteopetrosis due to severe function defect of osteoclasts. Moreover, Armstrong, A P. etc. 2002. J. Biol. Chem. Vol. 277(46) 44347-44356 discovered that mutating mouse gene, RANK, to make RANK lack binding sites of TFAF6 and let monocytes lose the ability of dividing to osteoclasts. It shows TRAF6 plays an important role in NF-κB activating RANKL/RANK signal transduction pathway.

Nuclear Factor κB, NF-κB

NF-κB will combine with inhibitory κB and maintains inactive condition under non-stimulating condition. When NF-κB is activated by RANKL, RANKL will combine with RANK and stimulate NF-κB to activate through TRAF6. The activation of NF-κB lead to phosphorylation on IκB at Ser-32 and Ser-36 by IκB kinase, IKK, and then the NF-κB proceeds hydrosis to separate from IκB. After that, the NF-κB will enter an nucleus to induce many genes relating to a dissolution activity of osteoclasts.

Mitogen-Activated Protein Kinases, MAP Kinase, MAPK, Pathway

The members of mitogen-activated protein kinases, MAP kinase or MAPK, family include extracellular signal-regulated kinase, ERK, p38-MAPKs, and c-Jun N-terminal kinase, JNK. It is known that p38's inhibitor, SB203580, or ERK's inhibitor, PD98059, both can inhibit induction of osteoclasts' differentiation and osteoclastogenesis by RANKL. The activation of ERK and JNK will affect the function of downstream transcription factor, activator protein-1, AP-1. ERK can induce and active the expression of c-Fos protein which is one of AP-1 family. Moreover, JNK can control the production of osteoclasts by phosphorylating c-Jun and enhancing transcription activities of Ap-1.

Src/PI3K/Akt Pathway

Src interacting with TRAF6 plays an important role in RANKL activating anti-apoptotic serine/threonine kinase, Akt. Src binds on the tail of RANL of cytoplasm and is activated by the stimulation that RANKL binds on RANK and TRAF6. Then, Src activates down stream, Akt. Moreover, in the process that Src activates Akt, the medium of phosphatidylinositol 3-kinase, PI3K, is needed. Using Src inhibitor, removing Sre gene or using LY294002 which is the inhibitor of PI3K can inhibit the activation of Akt induced by RANKL. RANKL/RANK regulates the surviving ability of osteoclasts through TRAF6 via the signal pathway of Src/PI3K/Akt.

Transcription Factors

RANKL/RANK signal pathway stimulates many osteoclast dissolution related gene expressions via activating transcription factor, AP-1, and NF-κB. In Ap-1 family, c-Jun, JunB, c-Fos, Fra-1 and Fra-2 participate in the regulation of generating osteoclasts. Furthermore, after c-Fos interacts with transcription factor such as nuclear factor of activated T cells, NFATc1, it stimulates the expression of the osteoclast dissolution genes, TRAP and Cathepsin K. Takayanagi, H. et al in 2007, Ann. NY Acad. Sci. No. 1116, Page 227-237: By calcium/calmodulin signal transduction of the up stream, after inner cellular calcium binds to calcium binding protein, calmodulin, first, it activates calcium/calmodulin-activated kinases, CaMKs and calcinerurin to make NFATc1 active. Therefore, Ap-1, NFATc1 and NF-κB are key transcription factors of regulating osteoclast dissolution.

Pro-Inflammatory Cytokines

Such as TNF-α, interleukin-1 (IL-1) and IL-6 can promote inflammation to induce the generation of osteoclasts. TNF-α which is released by active T cells and macrophages can promote the expression of RANK and increase the sensitivity of RANK for RANKL. Under inflammation, IL-6, IL-11 and IL-17 promote bone loss. However. Wei, S. et al in 2008, Pathol. Res. Pract. Section 204 (10), pages 695-706 found that IL-4, IL-10, IL-12, IL-18 and interferon-yby inhibiting osteoclast differentiation and the dissolution activity thereof to inhibit the formation of osteoclasts in vivo and in vitro.

High-Mobility Group Box 1, HMGB1

HMGB 1 is a protein in Eukaryotic cell nucleus. When macrophages are activated or influenced by pro-inflammatory cytokines, HMGB 1 will transfer to cytoplasm from nucleus, and then it will be moved out of cell by exocytosis or cell membrane break. Zhou, Z. et al in 2008, J. Bone. Miner. Res. Vol. 23(7), page 1084-1096 found that extracellular HMGB1 is similar to pro-inflammatory cytokines and promotes the bone loss under inflammatory conditions.

Monosodium Iodoacetate, MIA

Monosodium iodoacetate, MIA, is the glyceraldehyde-3-phosphate dehydrogenase, GAPDH, inhibitor, and in vitro, it can inhibit glycolysis to cause death of chondrocyte cells. In vivo, to inject MIA into knee joint cavities can induce the death of chondrocyte cells of knee joints to cause osteoarthritis. Under inflammatory environments, lymphocytes, macrophages and mast cells are infiltrated, and these cells release pro-inflammatory cytokines to activate osteoclasts, and then it promotes the bone loss of articular cartilage and subchondral bone.

With theophylline structure, KMUP-1 which is modified by the chlorophenyl is with the chemical name, 7-[2-[4-(2-Chlorophenyl) piperazin-1-yl]ethyl] theophylline. The theophylline structure is as Formulation 1, and the structure of KMUP-1 is as Formulation 2.

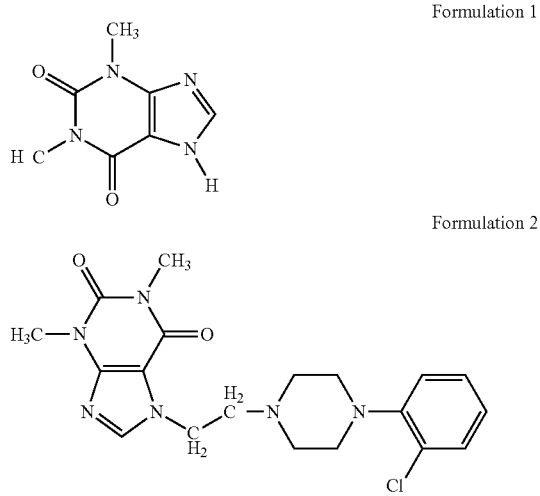

Formulation 1

Formulation 2

It is known that KMUP-1 has abilities of activating eNOS of epitheliums and endothelium, partial activating smooth muscle soluble guanylyl cyclase, sGC, inhibiting 3', 4' and 5'-phosphodiesterase, PDE, to increase on the amount of intercellular cGMP and opening potassium channels. Furthermore, KMUP-1 can induce the caversonal smooth muscle of rabbits' penises to be relaxed via stimulating the mechanism of cGMP and opening potassium channels. Besides, KMUP-1 has been proved that it can influence cAMP/PKA and cGMP/PKG pathway to cause the increase of the amount of tracheal epithelium's NO and to further activate the sGC in tracheal smooth muscle cells. Or KMUP-1 directly activates the sGC of smooth muscle cells to increase the amount of cGMP and activate PKG. KMUP-1 can also directly activate adenylate cyclase to induce the increase in the amount of cAMP to activate PKA. PKA and PKG both can cause the opening of potassium channels of smooth muscle cell membrane to make tracheal smooth muscle relaxed eventually. cAMP and cGMP are second transduction factors and can also control many physiological responses which include cell growth, cell differentiation, apoptosis, glycolysis, ester hydrolysis, immunization and inflammation, Miyamoto, K. et al in 1997, Biochem. Pharmacol. 54 (5), Page 613-617 found that in Walker256/S-bearing rat model, PDE4 inhibitors can inhibit the bone loss; Yoshimura, T. et al in 1997, Gen. Pharmacol. Vol. 29 (4), Page 633-638 are also considered that the proliferation of the key cytokines, TNF-α, IL-1 and IL-6, of bone loss can be inhibited by PDE4.

SUMMARY OF THE INVENTION

One of the purposes of the present invention is to offer a pharmaceutical composition for treating osteoporosis.

According to the aspect of the present invention, the present invention offers an effective amount of theophylline derivative which is modified by the chlorophenyl and can be synthesized by applying N-(2-chlorophenyl) piperazine and 7-(2-bromoethyl)theophylline. The theophylline derivative is with a chemical name, 7-[2-[4-(2-Chlorophenyl) piperazin-1-yl]ethyl]theophylline.

According to the above-mentioned aspect of the present, using the model of RANKL inducing macrophages to become osteoclast-like cells to discuss the influence of the phosphodiesterase 3, 4, 5 (PDE3, 4, 5) inhibitor, KMUP-1, on osteoclast-like cells' proliferation and differentiation and also discuss the mechanism thereof.

According to the second aspect of the present invention, in vitro, KMUP-1 has the function of inhibiting the proliferation and the differentiation of osteolast-like cells. In vivo, KMUP-1 can prevent and treat inflammatory diseases of joints. Therefore, KMUP-1 can be used as a new drug for preventing and treating bone loss.

Influence the proliferation of RAW264.7 via RANKL stimulating KMUP-1

RANKL can induce cell proliferation. KMUP-1 is double confirmed if it can inhibit the proliferation of RAW264.7 via MTT assay and BrdU assay. Both the MTT assay in FIG. 1 and BrdU assay in FIG. 2 show that KMUP-1 with 5 μM, 7.5 μM, 10 μM can inhibit the cell proliferation induced by RANKL. Besides, theophylline and with 10 μM have no previous inhibiting effect on cell proliferation induced by RANKL.

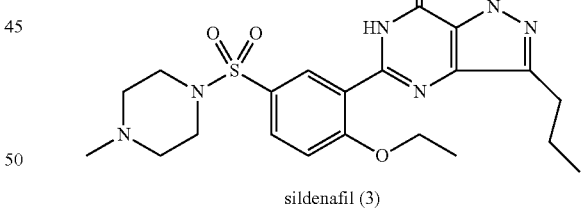

sildenafil (3)

Stimulating RAW264.7 to differentiate into osteoclast-like cells via RANKL is influenced by KMUP-1

Mononuclear cells, RAW264.7, are stimulated by RANKL to differentiate into multinuclear cells, osteoclast-like cells and secrete the target enzyme, TRAP, with dissolution activity. Mononuclear cells, RAW264.7, are stimulated by RANKL for 5 days, and are observed the cell differentiation with a optical microscope, the differentiation of osteoclast-like cells and the influence of KMUP-1 are confirmed by TRAP staining method and TRAP activity test on the fifth day. According to the staining result, it is discovered that in the control group, the cells are all small mononuclear macrophages. Because TRAP is not expressed, the cells cannot express peach-red color after TRAP staining. However, in the RANKL group which is induced by 10 ng/ml RANKL for 5 days, many differentiated big multinuclear osteoclast-like cells are peach-red colors as showed in FIG. 3 that the group which is administrated with KMUP-1 obviously express inhibition phenomenon related to dose. From the result of TRAP activity test, the cells which are induced by 10 ng/ml RANKL for 5 days express high activity, but as showed in FIG. 4 that the group which is administrated KMUP-1 can be inhibited, and the inhibiting effect is related to dose. Besides, 10 μM theophylline and sildenafil have no obviously inhibiting effect on TRAP activity induced by RANKL.

The Influence of KMUP-1 to the Dissolution of Osteoclast-Like Cells

As showed in FIG. 4 that KMUP-1 can efficiently inhibit the differentiation of osteoclast-like cells. In order to confirm the influence of KMUP-1 to the bone dissolution of differentiated osteoclast-like cells, cells are cultured in the plates which are coated calcium phosphate of bone-like matrix in the bottom and are given 10 ng/ml RANKL for five days and different concentration of KMUP-1. According to the result, compared with the control group, in the group which is given 10 ng/ml RANKL alone for 5 days, the osteoclast-like cells have obviously dissolution activity, so the covers at the plate bottom present many holes. Furthermore, the group which is administrated KMUP-1 can inhibit the dissolution of osetocalst-like cells. And FIG. 5 shows that after measuring the dissolution area, it is found that the inhibiting effect of KMUP-1 is dose dependent. It shows that KMUP-1 cannot only decrease the differentiation of osteoclast-like cells, reduce generation of TRAP enzyme but also inhibit the dissolution of osteoclast-like cells.

KMUP-1 influences that RAW264.7 cells secrete pro-inflammatory cytokines stimulated by RANKL.

Under RANKL stimulation, mononuclear RAW264.7 cells can secrete pro-inflammatory cytokines such as TNF-α, IL-1, IL-6, etc. ELISA is used to measure that KMUP-1 influences RANKL to induce the secretion of pro-inflammatory cytokines. As showed in FIG. 6 to FIG. 7(A), RANKL induces macrophages to secrete the pro-inflammatory cytokines, TNF-α, IL-1, IL-6, and KMUP-1 presents a dose dependent inhibition phenomenon. Besides, as showed in FIG. 7(B), increase the dose of KMUP-1 can raise the amount of anti-inflammatory cytokines, IL-10.

KMUP-1 influences the activation of NF-κB pathway induced by RANKL.

IκBα which originally binds with NF-κB to inhibit its activity in cytoplasm is stimulated by RANKL to be phosphorylized and be hydrolyzed after separating from NF-κB. Then, the free NF-κB transfers into a cell nucleus to play a role as a transcription factor. According to the experimental result, compared with the control group, in the group induced by RANKL for 30 minutes, the IκBα in the cytoplasm is obviously phosphorylized and hydrolyzed. As showed in FIG. 8(A), the group that is administrated different concentrations of KMUP-1 in advance to react 24 hours can inhibit the effect of RANKL. On the other hand, compared with the control group, in the group induced by RANKL for 30 minutes, the amount of p65 in the cell nucleus is obviously increased. As shown in FIG. 8(B), the group that is administrated different concentrations of KMUP-1 in advance to react 24 hours has the inhibiting effect on that p65 enters into a cell nucleus, and the expression of PARP in the cell nucleus is not changed. According to the result, KMUP-1 can inhibit NF-κB activation induced by RANKL.

KMUP-1 influences the activation of MAP kinases pathway induced by RANKL.

MAP kinases including ERK, JNK and p38 are stimulated by RANKL to be phosphorylized and further influence the down-stream key transcription factors which induce the differentiation of osteoclast-like cells such as c-Fos, NFATc1, etc. Before estimating the drug effect, 10 ng/ml RANKL are used to induce the phosphorylation of ERK, JNK and p38 at different time points. By western blot, it is found that the phosphorylation is most obvious at 15 minutes, so 15 minutes is used to be the induced time of RANKL. As shown in FIG. 9 to FIG. 11, they are about the phosphorylation levels of ERK, JNK and p38 in the cytoplasm, and KMUP-1 can efficiently inhibit the phosphorylation of ERK, JNK and p38 induced by RANKL at 7.5 μM and 10 μM. It is shown that KMUP-1 can reduce the activation of MAP kinases induced by RANKL.

KMUP-1 influences RANKL activating the key transcription factors, c-Fos and NAFATc1.

It is known that KMUP-1 influences the activation of MAP kinases pathway induced by RANKL, and the down-stream key transcription factors which stimulate osteoclasts to differentiate such as c-Fos and NFATc1 should be estimated if they are also inhibited by KMUP-1. As shown in FIG. 12, the expression of c-Fos is induced by RANKL for 24 hours, and KMUP-1 can efficiently inhibit it at higher concentration, 7.5 μM and 10 μM. As shown in FIG. 13, from the result of the western blot, 5 μM, 7.5 μM and 10 μM KMUP-1 can efficiently inhibit the expression of NFATc1 induced by RANKL for 24 hours. It is shown that KMUP-1 can efficiently inhibit MAP kinases serial signal pathway at higher concentration.

KMUP-1 influences that RANKL induces cellular calcium influx and the activation of calcineurin.

The key transcription factor, NFATc1, is affected by MAP kinases/c-Fos and also influenced by the calcium pathway. After RANKL stimulating to cause the cellular calcium influx, the increase of the inner-cellular calcium will activate the expression of the down-stream calcinuerin, and the activation of the calcinuerin is related to the transcription factor, NFATc1. Examining the changes of inner-cellular calcium concentration and western blot are used to estimate the expression of calcinuerin proteins. Macrophages, RAW264.7, are stimulated by RANKL for 4 minutes, and a fluorescent probe of calcium (fura-2/AM) is used to exam the inner-cellular calcium. As shown in FIG. 14(A), the concentration of the inner-cellular calcium dose not change obviously. In the cell culture, the stimulation of RANKL is applied in advance for one week to make macrophages to differentiate into osteocalast-like cells, OCL, and then the osteoclast-like cells are stimulated by RANKL can obviously increase the concentration of inner-cellular calcium. 0.1 μM KMUP-1 cannot apparently inhibit RANKL inducing extracellular calcium influx, but 1 μM and 10 μM KMUP-1 can inhibit it (FIGS. 14 and 15). Stimulated by RANKL for 24 hours, as shown in FIG. 16 is a result of a western blot, it is shown that compared with the control group, the expression of the calcineurin increases obviously. Moreover, given different concentrations of KMUP-1 at the same time, it is found that 5 μM, 7.5 μM and 10 μM KMUP-1 can obviously inhibit the expression of calcineurin induced by RANKL.

KMUP-1 Influences the Phosphorylation of Akt Induced by RANKL.

RANKL can activate PI3K/Akt pathway to maintain the existence and the proliferation of osteoclast-like cells and prevent the apoptosis. The Akt phosphorylation level which is induced by RANKL is examined at different time points. The induced Akt phosphorylation is most apparent when it is induced by 10 ng/ml RANKL for 30 minutes. Therefore, 30 minutes are used to be the time point for inducing Akt phosphoryaltion. As shown in FIG. 17, KMUP-1 can efficiently inhibit phosphorylation of Akt induced by RANKL, and the inhibition is dose dependent.

KMUP-1 influences the activation of MMP-2 and MMP-9 induced by RANKL.

KMUP-1 influences there major up-stream signal transduction pathways which are related to RANK/RANKL. Western blot is used to estimate the amount of matrix metalloproteinase (MMP)-2 and MMP-9 which are related to the amplify and quantify its mRNA. RAF6, TRAP, c-Fos, NFATc1, MMP-9, Fra-1, Fra-2, c-Src and Cathepsin K can be induced by 10 ng/ml RANKL, and KMUP-1 inhibits the mRNA expression of TRAP, c-Fos, NFATc 1, MMP-9, Fra-1 but not obviously inhibits TRAF6, Fra-2, c-Src and Cathepsin K (Table 1). Besides, the western blot as shown in FIG. 25, it is found that KMUP-1 has no obvious effect on that 10 ng/ml RANKL induces the protein expression of TRAF6.

TABLE 1

Effect of KMUP-1 on RANKL-induced mRNA expression levels of resorption-related genes in RAW264.7 cells.

| Gene | CTL | RANKL 10 ng/ml + KMUP-1 | | | | | |
|---|---|---|---|---|---|---|---|
| | | 0 | 1 µM | 2.5 µM | 5 µM | 7.5 µM | 10 µM |
| TRAF6 | 100% | 124.3 ± 5.6%[a] | 100.2 ± 4.7% | 123.8 ± 2.3% | 125.9 ± 2.9% | 128.4 ± 6.5% | 127.2 ± 1.3% |
| TRAP | 100% | 430.7 ± 28.7%[a] | 422.4 ± 24.8% | 427.7 ± 39.3% | 359.9 ± 20.7%[b] | 293.8 ± 30.1%[b] | 259.3 ± 18.3%[b] |
| c-Fos | 100% | 114.7 ± 6.8%[a] | 105.4 ± 8.1% | 100.3 ± 4.7% | 84.5 ± 5.2%[b] | 67.1 ± 4.5%[b] | 73.1 ± 6.3%[b] |
| NFATc1 | 100% | 280.5 ± 8.8%[a] | 256.9 ± 7.5% | 184.7 ± 4.2%[b] | 161.8 ± 2.9%[b] | 132.9 ± 2.4%[b] | 121.5 ± 4.5%[b] |
| MMP-9 | 100% | 1824.2 ± 159.6%[a] | 1732.4 ± 168.9% | 1619.9 ± 179.8% | 1570.9 ± 159.3%[b] | 1439.8 ± 188.8%[b] | 1372.0 ± 175.6%[b] |
| Fra-1 | 100% | 437.9 ± 29.1%[a] | 244.1 ± 38.9%[b] | 285.1 ± 44.8%[b] | 310.1 ± 56.3%[b] | 238.7 ± 49.9%[b] | 265.2 ± 64.1%[b] |
| Fra-2 | 100% | 472.2 ± 30.1%[a] | 428.3 ± 38.5% | 490.5 ± 42.3% | 488.2 ± 57.6% | 474.5 ± 52.1% | 496.6 ± 44.1% |
| c-Src | 100% | 91.2 ± 3.3% | 101.4 ± 4.5% | 103.9 ± 2.7% | 95.8 ± 2.8% | 91.5 ± 4.5% | 98.6 ± 6.2% |
| Cathepsin K | 100% | 303 ± 5.6%[a] | 304 ± 7.8% | 305 ± 5.9% | 312 ± 6.2% | 321.5 ± 10.2% | 245 ± 8.5%[b] |

RAW264.7 cells were treated with RANKL and KMUP-1 for 24 hoursr. Total RNA was extracted and the level of expression of the mRNA of the indicated genes was analyzed by RT-PCR. The results are reported as mean ± SEM.
[a] $P < 0.05$ versus control group (CTL),
[b] $P < 0.05$ versus RANKL group.

dissolution of osteoclast-like cells, and the enzyme activity of MMP-2 and MMP-9 are estimated via Gelatin Zymography. As shown in the western blot of FIG. 18 and FIG. 19, KMUP-1 can efficiently inhibit the amount of MMP-2 and MMP-9 proteins which are induced by RANKL for 24 hours. As shown in FIG. 20 and FIG. 21, 10 µM KMUP-1 can reduce the enzyme activity of MMP-2 and MMP-9 which are induced by RANKL for 24 hours.

The influence of KMUP-1 on that RANKL induces HMGB1 to transfer to extracellular space from a cell nuclear.

HMGB1 can affect the proliferation and differentiation of osteoclasts, the HMGB1 which originally exists in a cell nuclear is stimulated by RANKL to transfer to cytoplasm or extracellular space, and the HMGB1 in the extracellular space like pro-inflammatory cytokines can regulate the proliferation and differentiation of osteoclasts via RANK/RANKL pathway or other pathways. 10 ng/ml RANKL is used to stimulate RAW264.7 cells, and the extracellular medium, cytoplasm and nucleus are separated at 0 hours, 6 hours, 12 hours, 18 hours and 24 hours, and then via western blot to confirm the expression level of the HMGB1. After stimulating 24 hours, the HMGB1 obviously transfers to the extracellular space from the nucleus and the cytoplasm (FIGS. 22(A), 23(A), and 24(A)). Moreover, when it is stimulated by RANKL for 18 hours, the effect of transferring to the extracellular space and the cytoplasm is most obvious. Different concentrations of KMUP-1 are administrated for 24 hours, and 10 ng/ml RANKL is used to stimulate for 18 hours. As shown in FIGS. 22(B), 23(B), and 24(B), given 5 µM, 7.5 µM and 10 µM KMUP-1 all can inhibit that RANKL induces HMGB1 to transfer to extracellular space from a cell nuclear, and the inhibition is dose dependent.

KMUP-1 influences that RANKL induces the expression of genes' mRNA related to bone dissolution activities.

RANKL can induce many genes' expression related to bone dissolution activities. Reverse transcription-polymerase chain reaction, RT-PCR, is used to extract RNA of cells, KMUP-1 influences that MIA induces the prevention and treating of knee arthritis in rat model.

Injecting 4 mg/25 µl MIA physiological saline into rats' knee joints for days can induce knee arthritis. Because the regulation of pro-inflammatory cytokines stimulate the activity of osteoclasts, it causes gradual loss of articular cartilage and subchondral bone. 1 mg/kg, 2.5 mg/kg and 5 mg/kg are orally administrated in advance for one week, and after that, the 4 mg/25 µl MIA physiological saline is injected into the knee joints of the rats on the eighth day, and then the 1 mg/kg, 2.5 mg/kg and 5 mg/kg are orally administrated again for one week, and the animals are sacrificed on the fifteenth day.

7 days after injecting the MIA physiological saline, the articular cartilage has obvious damages, and compared with the Sham group, it is very unsmooth. However, the group which is administrated 2.5 mg/kg and 5 mg/kg KMUP-1 to prevention and treating can reduce the damages caused by the MIA.

From the result of the slices of Hematoxylin and Eosin (H&E) stain, the cartilage tissues of the sham group is undamaged, but the group which is administrated the MIA physiological saline alone can be obviously observed the holes and a great amount of inflammatory cell infiltrations which are caused from the defects and damages of the cartilage tissues. In the group with 1 mg/kg KMUP-1 for prevention and treating, the holes and defects from the damages of the MIA still exist. The holes and the area of the damaging cartilage tissues present the trend of becoming smaller, but there are still many inflammatory cell infiltrations. Compared with the group with 1 mg/kg KMUP-1, the holes and defects of the cartilage tissues from the damages of the MIA in the group with 2.5 mg/kg KMUP-1 become much better, and compared with the group damaged by the MIA, it presents obvious differences and the inflammatory cell infiltrations become less. In the group with 5 mg/kg KMUP-1, the holes and defects of the cartilage tissues from the damages of the MIA close to the recovery condition of the sham group, but there are still some inflammatory cell infiltrations. From the result of the H&E slices, it is found that KMUP-1 can prevent and treat the damages of the cartilage tissues caused by MIA, and the effect thereof is dose dependent.

Form the result of the toluidine blue slices, compared with the sham group, a great amount of mast cell infiltrations (dark blue) can be seen in the holes and defects of the cartilage tissues from the damages of the MIA. Furthermore, in the group which is given KMUP-1, the mast cell infiltrations present a trend of reducing according to the higher dose. It is shown that KMUP-1 can reduce the inflammation of knee joints, and the inhibiting effect is dose dependent.

An excipient or as called "pharmaceutically acceptable carrier or excipient" and "biologically available carrier or excipient" include solvents, dispersants, coatings, antibacterial agents, antifungal agents, saving absorbents, delaying absorbents and any other conventionally proper compounds. Usually, these carriers or excipients do not have the activities of treating diseases. Furthermore, the derivative disclosed in the present invention is mixed with the pharmaceutically acceptable carrier or excipient to prepare each drug which administrates to animals and humans will not cause any drug adverse reaction, allergy and any other unsuitable responses. Therefore, the derivative disclosed in the present invention mixed with the pharmaceutically acceptable carrier or excipient is suitable for clinical and humans. To apply the drugs of the derivative in the present invention on administrating via a vein, an oral, an inspiration, a nasal cavity, a rectum, a vagina, a hypoglossis can have treating effects. For different patients, they are administrated with about 0.1 g~100 mg active components each day.

The carriers are changed with the different drugs, the composition of sterile injection can be suspended in drug-free solutions of diluted intravenous fluid or solvents, and such solvents is 1,3-butanediol. During the injection, the acceptable carriers can be Mannitol or water. In addition to the fixed oil or synthetic single or double ester suspension medium is the generally conventional solvent. Fatty acids such as oleic acid, olive oil, castor oil, etc. or its glyceride derivatives, in particular the type of multi-oxygen-ethyl can be prepared for injections and is acceptable oils for natural medicine. These oil solutions or suspensions can contain diluents or dispersants of long-chain alcohol, carboxymethyl cellulose or similar dispersants. Other surfactants of general use such as Tween, Spans or other similar emulsifiers or pharmaceutical industry acceptable solid, liquid or other bio-available enhancer used in drug developments.

The composition for oral administration is adopted any orally acceptable drug, and the type thereof includes capsules, lozenges, tablets, emulsifiers, liquid suspensions, dispersants and solvents. The carriers generally used in oral drugs use tablets for example it can be lactose, corn starch, lubricants such as magnesium stearate as the basic additive. Moreover, the diluents used for capsules include lactose and dry corn starch. Forming liquid suspensions or emulsifiers is to suspect active materials or solve it in oil interfaces of the suspensions or binding emulsifiers. It is added suitable sweeter, seasonings or edible dye.

The composition of nasal inspirations or inhalations can base on the conventional preparation technology to produce. For example, the composition is solved in physiological saline, and benzyl alcohol or other suitable preservatives are added, or absorbsfacients are added to enhance bioavailability. The composition of the present invention also can be prepared into suppository for administering via a rectum or a vagina.

The composition of the present invention also can be applied on intravenous administrations which include via hypodermics, abdominal cavities, veins, muscle, or joint cavities, encephalic, synovial fluids, spinal injections, aortic injections, pleural injections, disorder sites injections or other suitable administrating technics.

Figure 1:
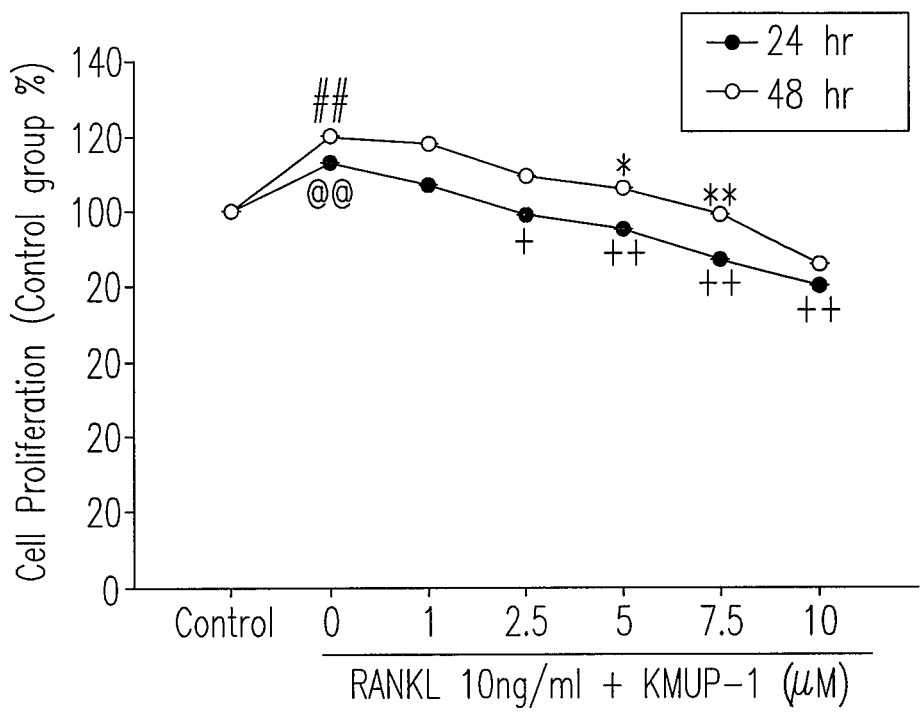
FIG. 1 KMUP-1 inhibited the proliferation induced by RANKL (MTT assay);
$P<0.01$ compared with the control group (24 hr);
@@$P<0.01$ compared with the control group (48 hr);
*$P<0.05$, **$P<0.01$ compared with the RANKL group (24 hr);
+$P<0.05$, ++$P<0.01$ compared with the RANKL group (48 hr)
Figure 2:
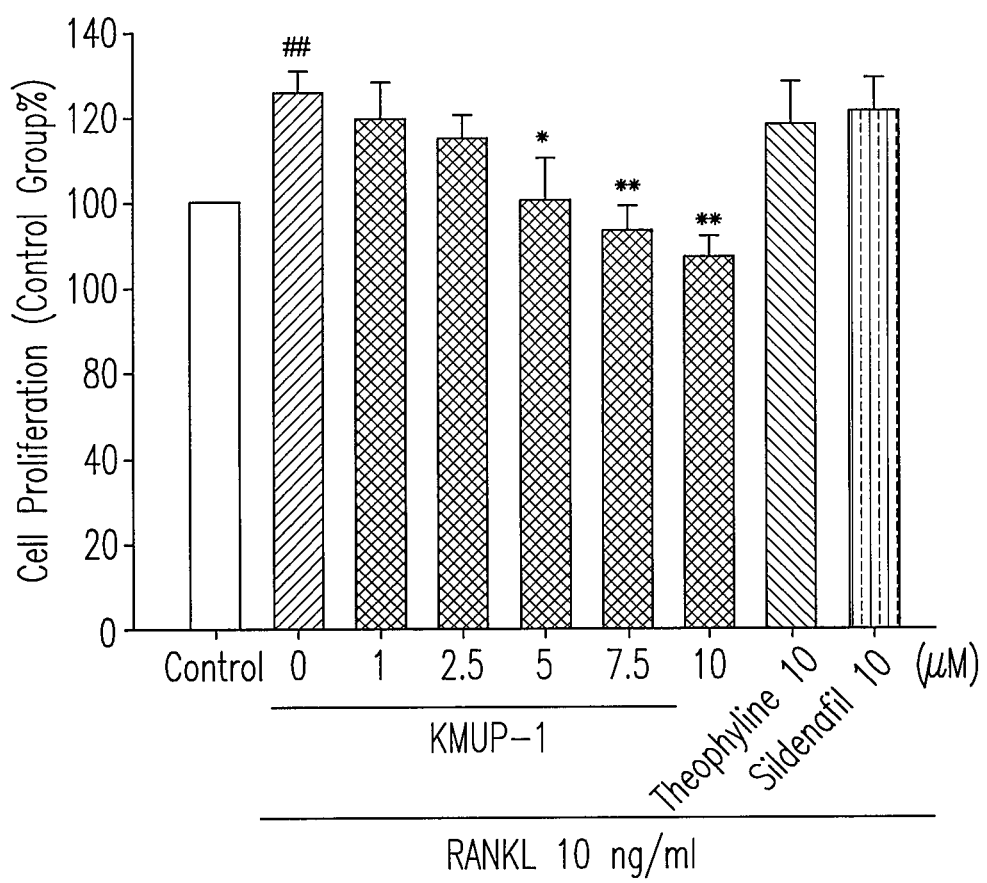
FIG. 2 KMUP-1 inhibited the proliferation induced by RANKL (MTT assay);
$P<0.01$ compared with the control group
*$P<0.05$, **$P<0.01$ compared with the RANKL group FIG. 3 KMUP-1 inhibited osteoclast-like cells to differentiate to multi-nuclear cells;
$P<0.01$ compared with the control group;
**$P<0.01$ compared with the RANKL group FIG. 4 KMUP-1 inhibited TRAP activity;
$P<0.01$ compared with the control group;
*$P<0.05$, **$P<0.01$ compared with the RANKL group FIG. 5 KMUP-1 reduced the area of dissolution;
$P<0.01$ compared with the control group;
**$P<0.01$ compared with the RANKL group FIG. 6 KMUP-1 influenced that RAW264.7 cells secrete pro-inflammatory cytokines stimulated by RANKL;
A) TNF-α
B) IL-1β
$P<0.01$ compared with the control group;
*$P<0.05$, **$P<0.01$ compared with the RANKL group FIG. 7 KMUP-1 inhibited the secretion of IL group pro-inflammatory cytokines;
A) IL-6
B) IL-10
$P<0.01$ compared with the control group;
*$P<0.05$, **$P<0.01$ compared with the RANKL group FIG. 8 KMUP-1 influenced the activation of NF-κB pathway of RAW264.7 cells induced by RANKL;
A) KMUP-1 inhibited the phosphorylation of IκBα
B) KMUP-1 reduced the amount of p65 in nuclei
$P<0.01$ compared with the control group;
*$P<0.05$, **$P<0.01$ compared with the RANKL group FIG. 9 KMUP-1 inhibited the phosphorylation of ERK;
$P<0.01$ compared with the control group;
*$P<0.05$, **$P<0.01$ compared with the RANKL group FIG. 10 KMUP-1 inhibited the phosphorylation of JNK;
$P<0.01$ compared with the control group;
*$P<0.05$, **$P<0.01$ compared with the RANKL group FIG. 11 KMUP-1 inhibited the phosphorylation of p38;
$P<0.01$ compared with the control group;
**$P<0.01$ compared with the RANKL group FIG. 12 KMUP-1 inhibited expression of c-Fos activated by RANKL;
$P<0.01$ compared with the control group;
**$P<0.01$ compared with the RANKL group FIG. 13 KMUP-1 inhibited expression of NFATc1 activated by RANKL;
$P<0.01$ compared with the control group;
*$P<0.05$, **$P<0.01$ compared with the RANKL group FIG. 14 KMUP-1 influenced that RANKL induced cellular calcium influx.
Figure 3:
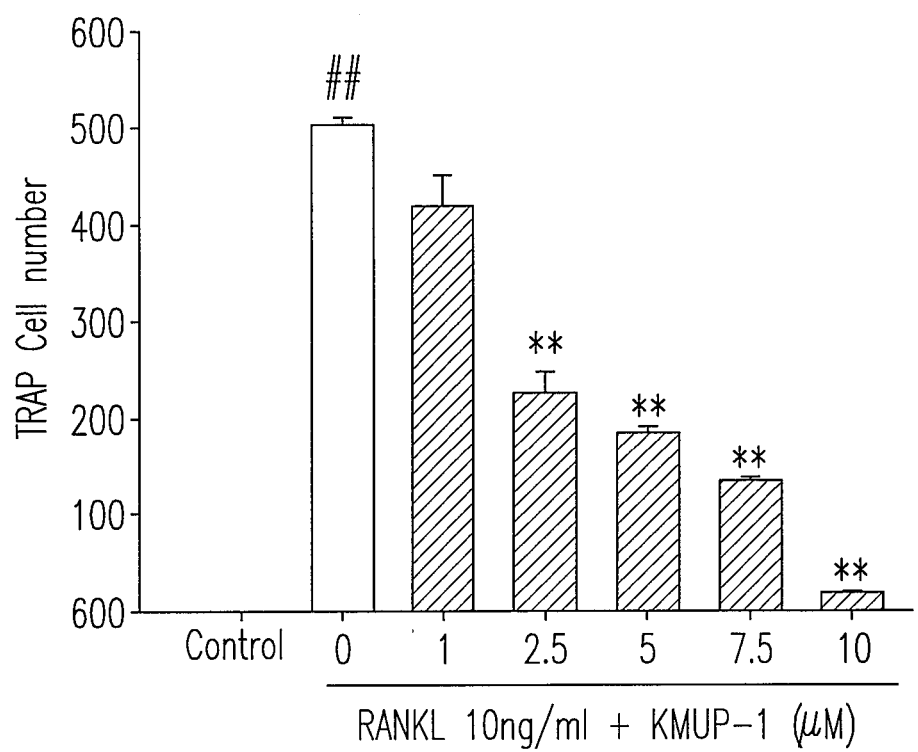
Figure 4:
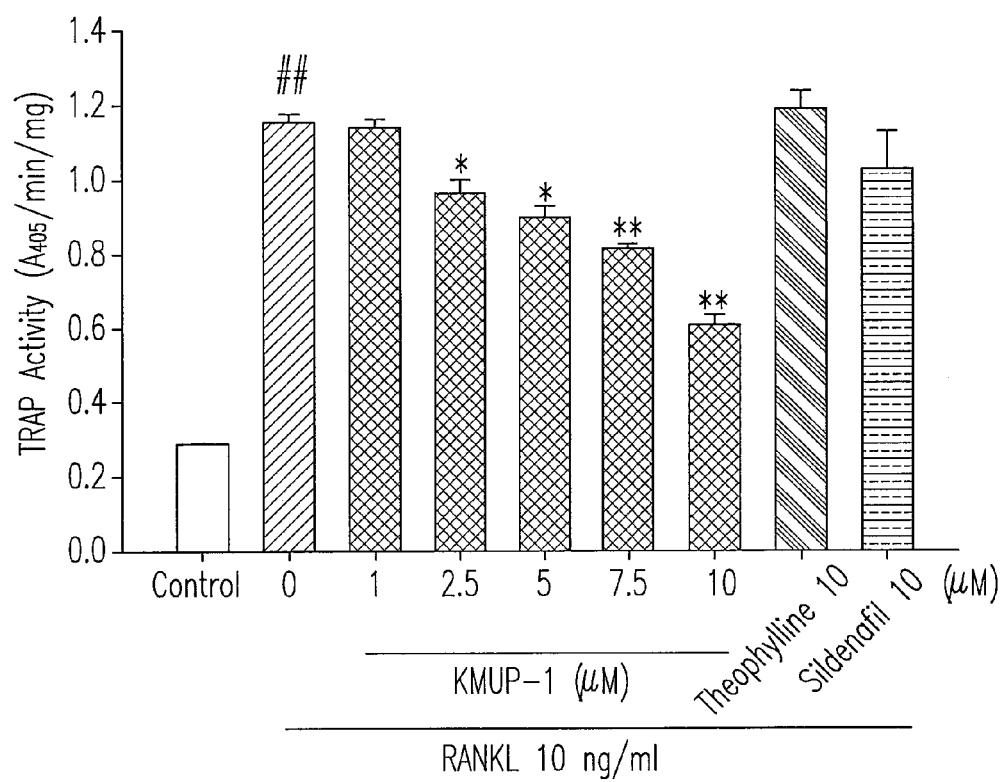
Figure 5:
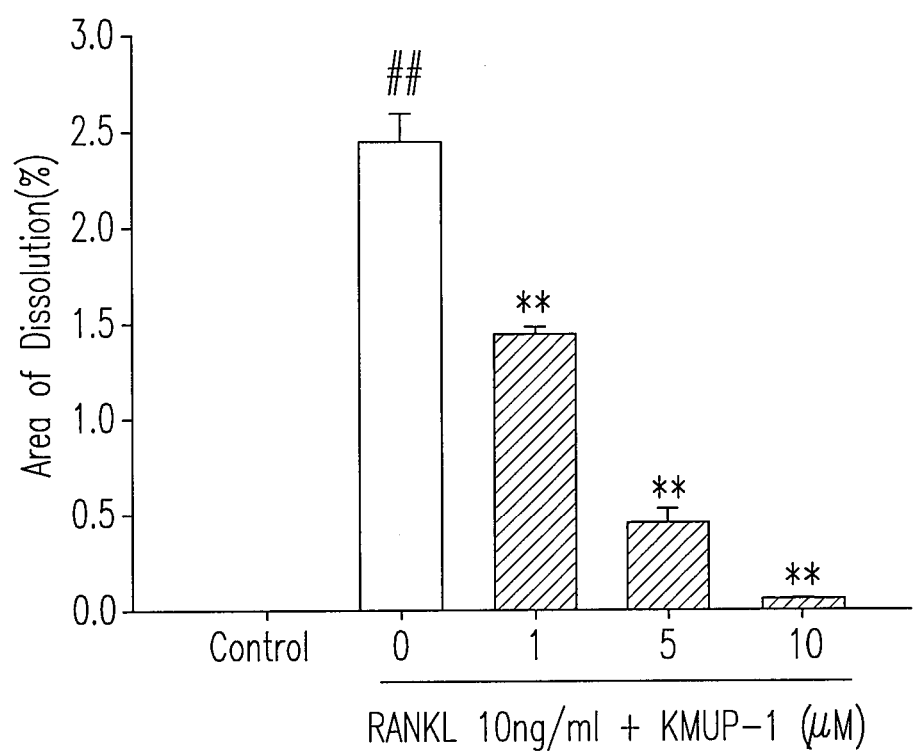
Figure 6A:
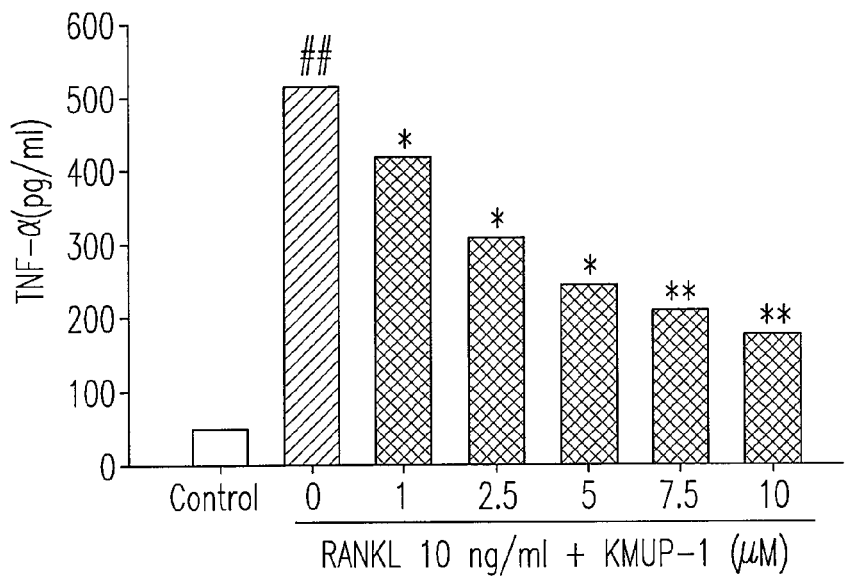
Figure 6B:
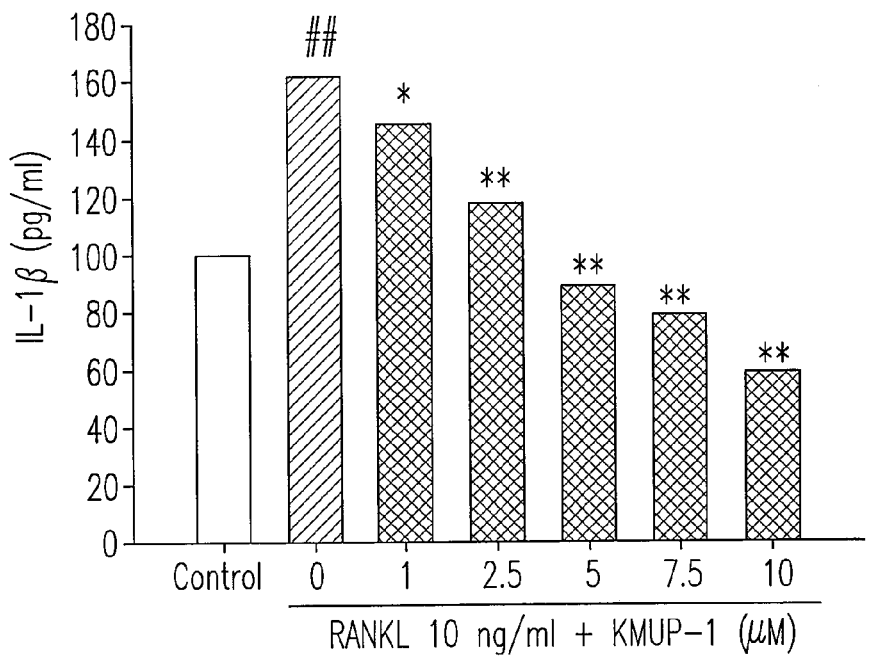
Figure 7A:
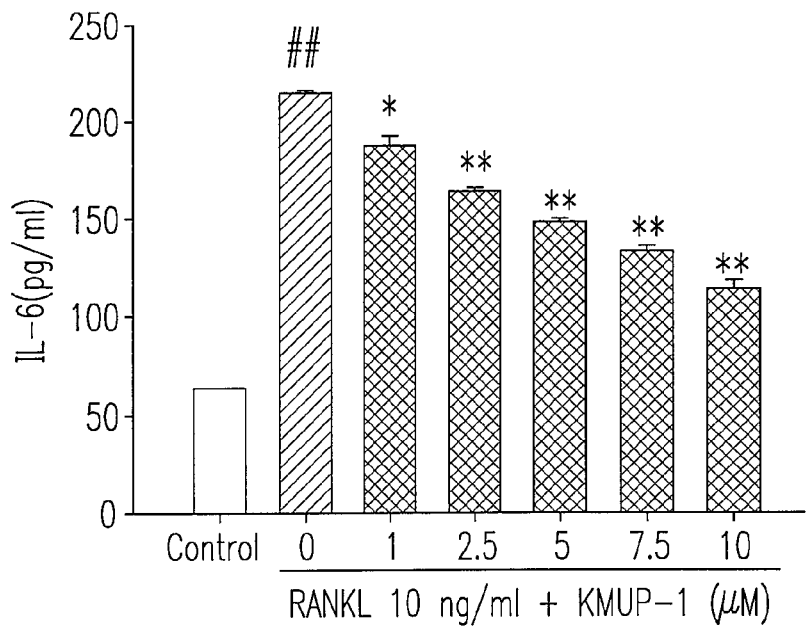
Figure 7B:
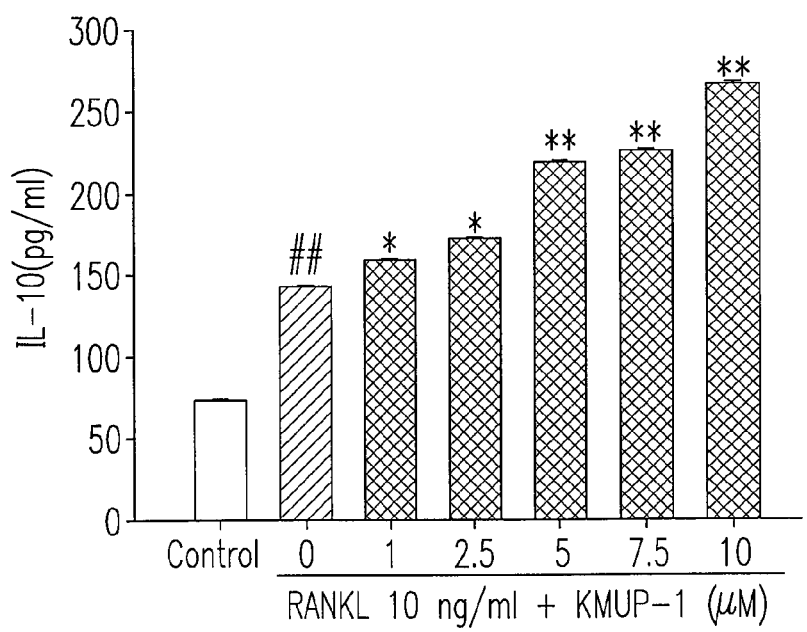
Figure 8A:
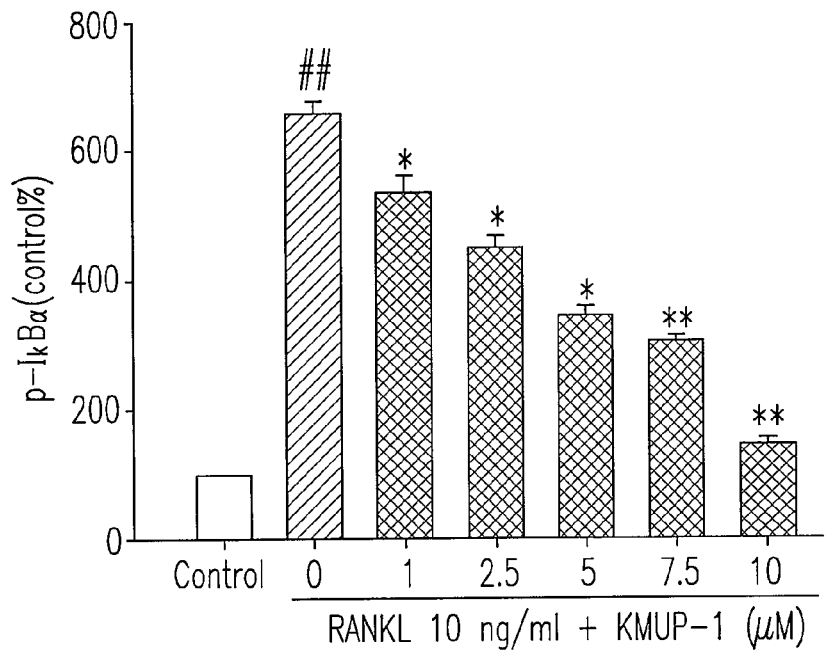
Figure 8B:
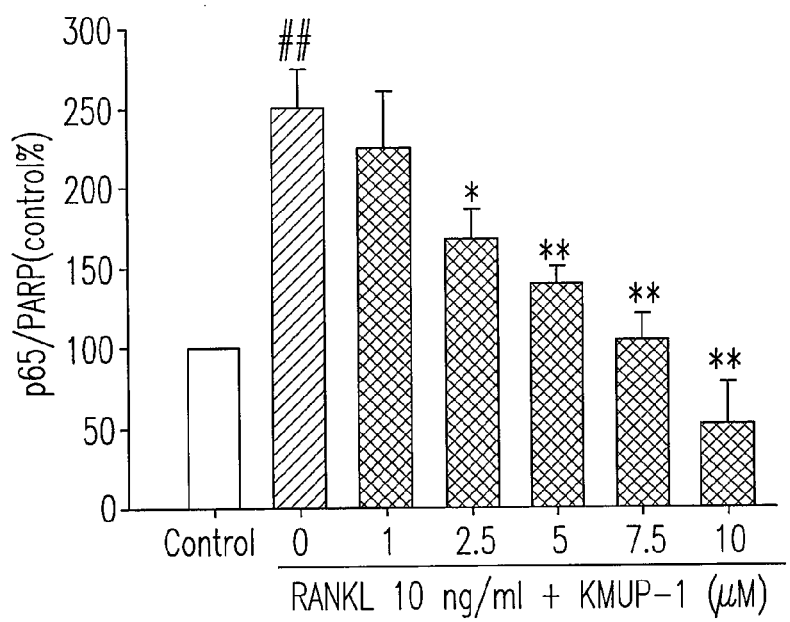
Figure 9:
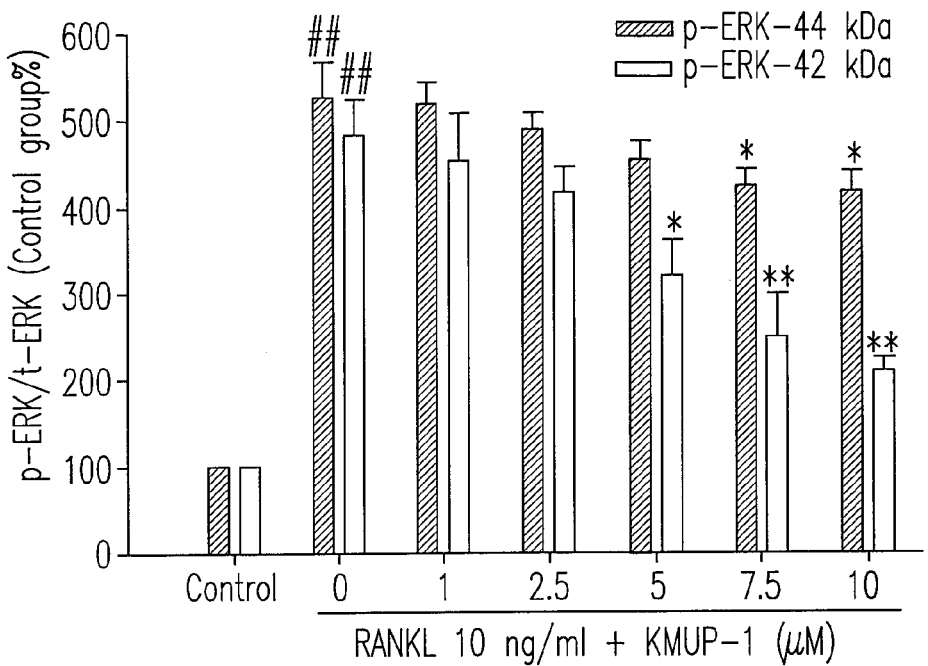
Figure 10:
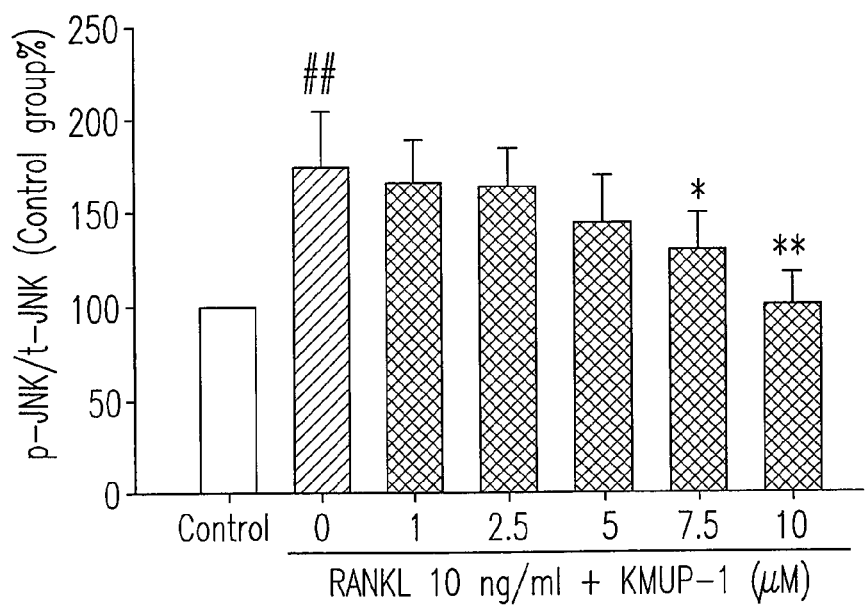
Figure 11:
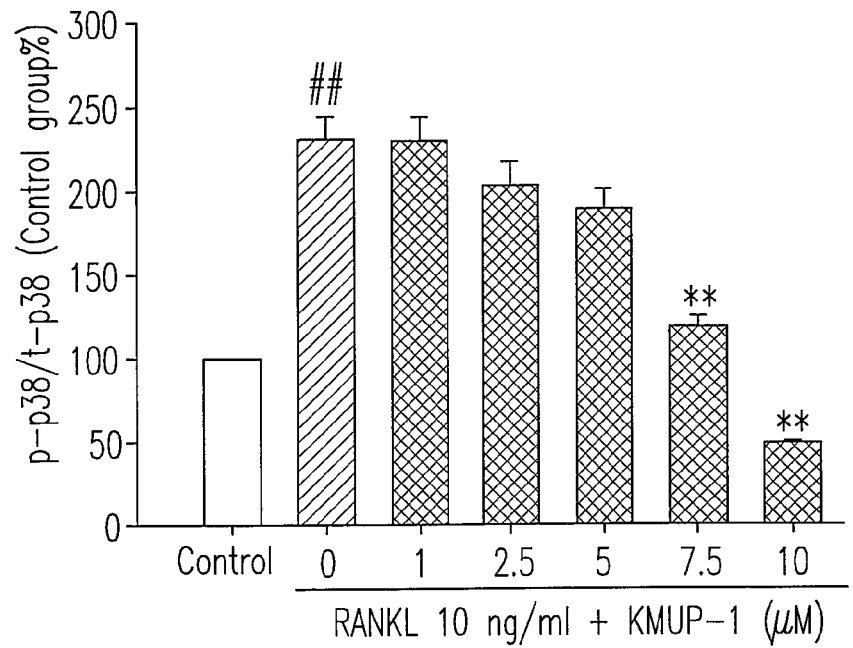
Figure 12:
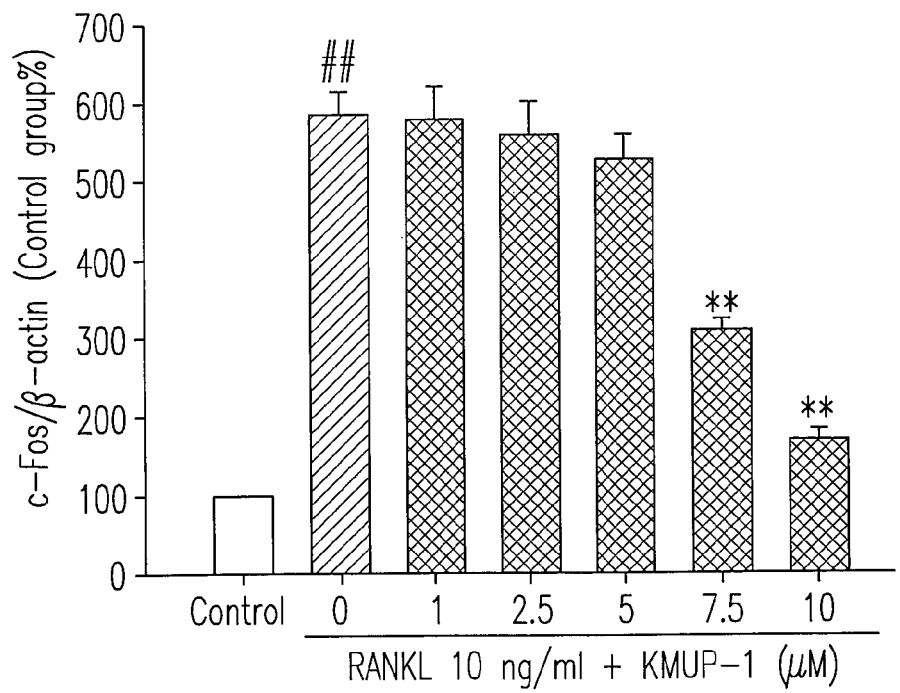
Figure 13:
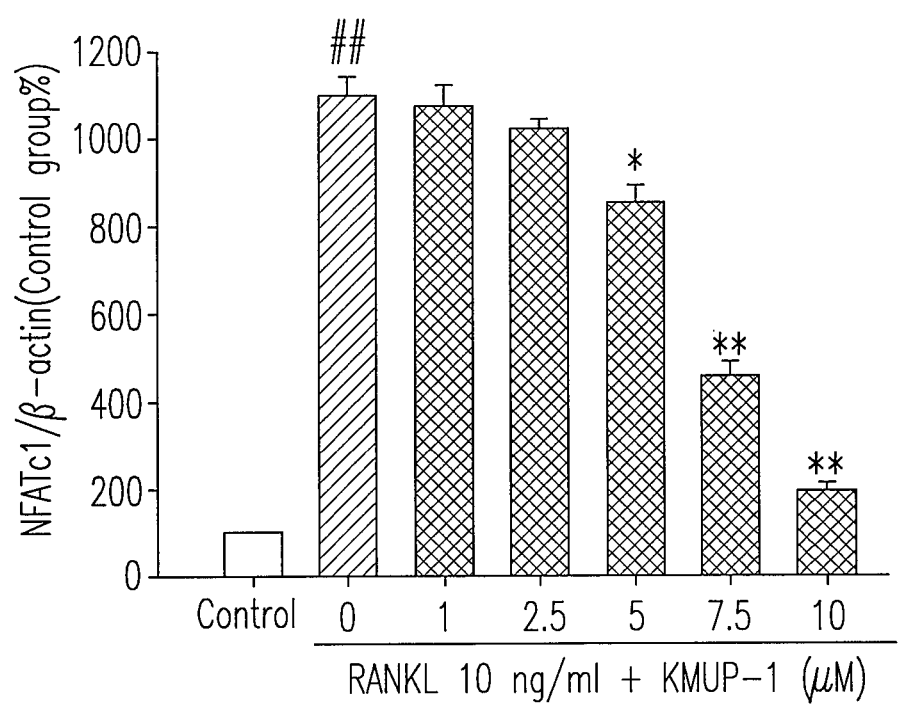
Figure 14A:
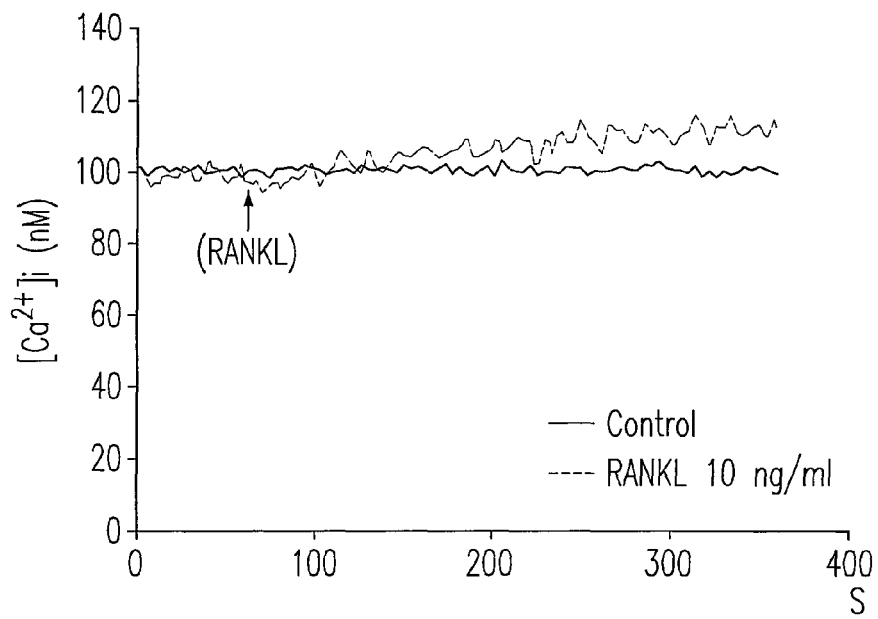
Figure 14B:
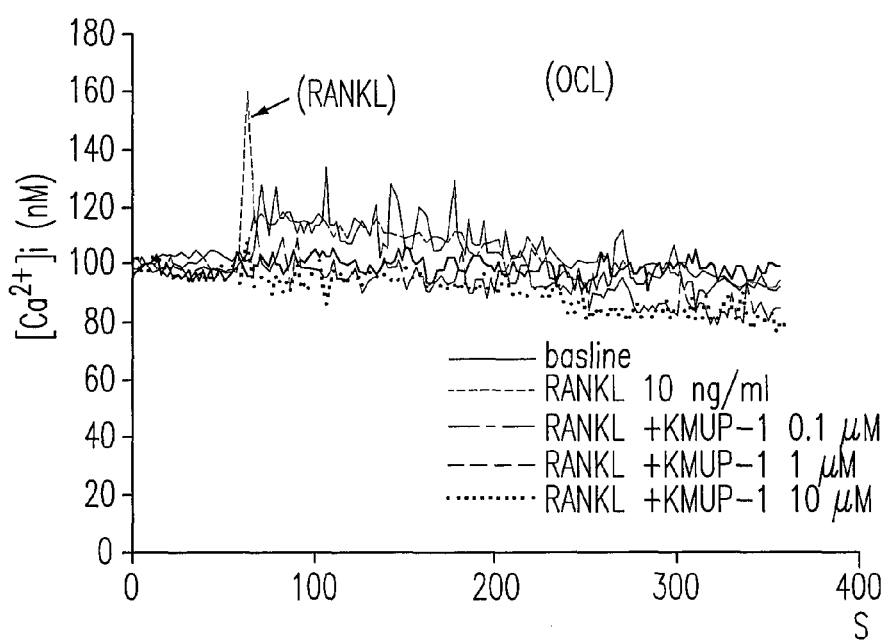
Figure 15:
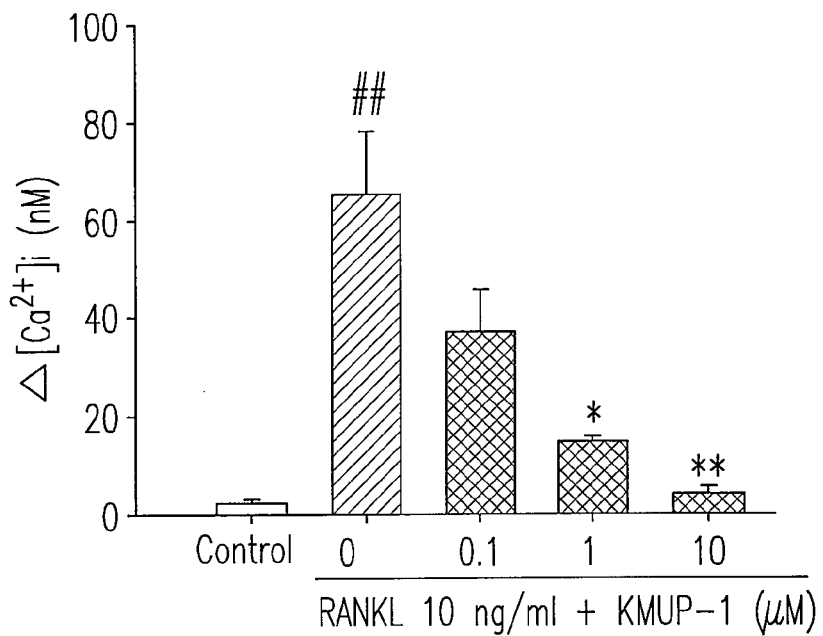
Figure 16:
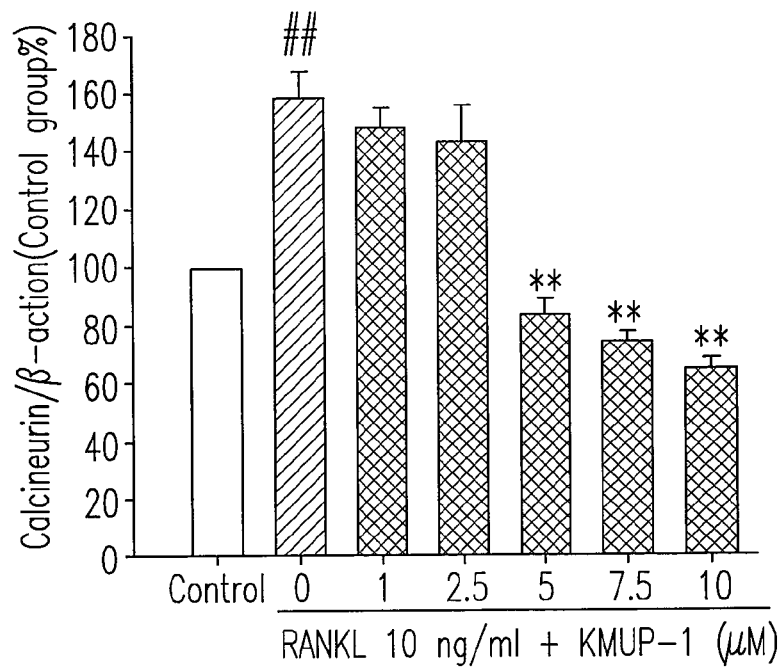
Figure 17:
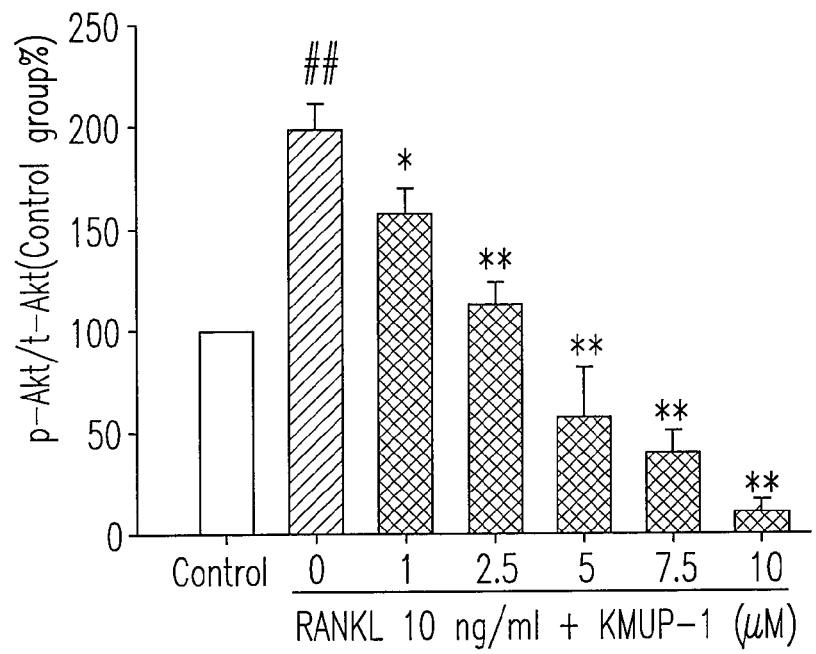
Figure 18:
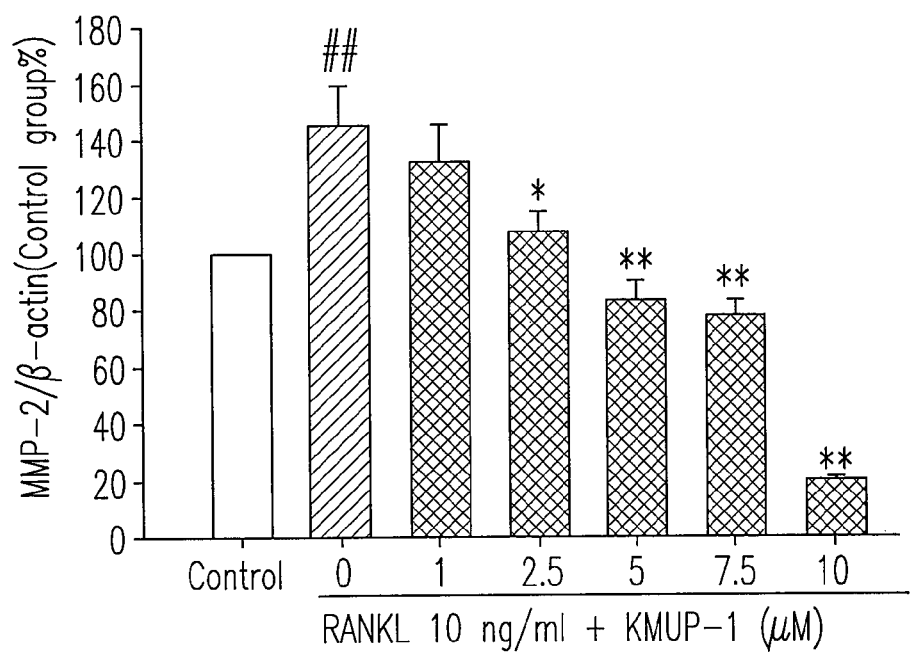
Figure 19:
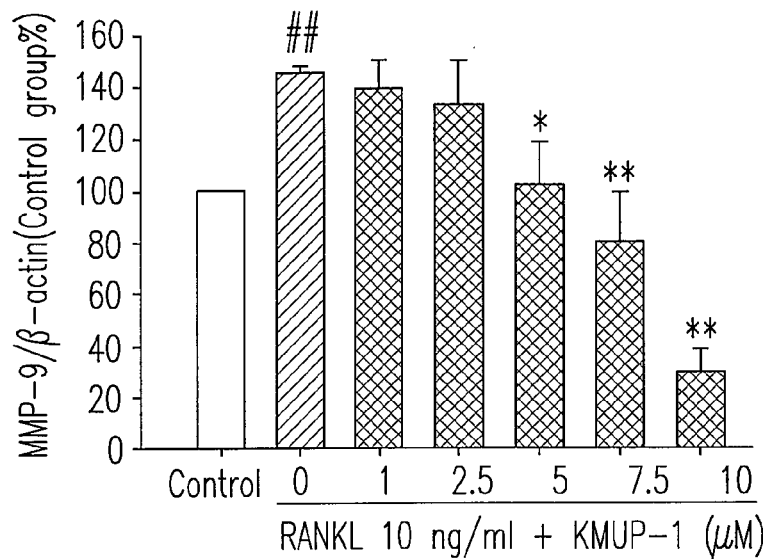
Figure 20:
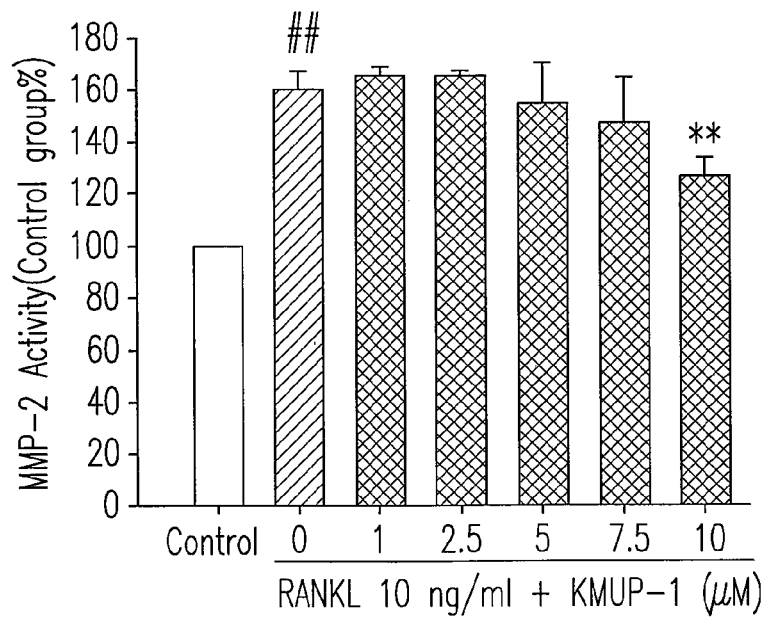
Figure 21:
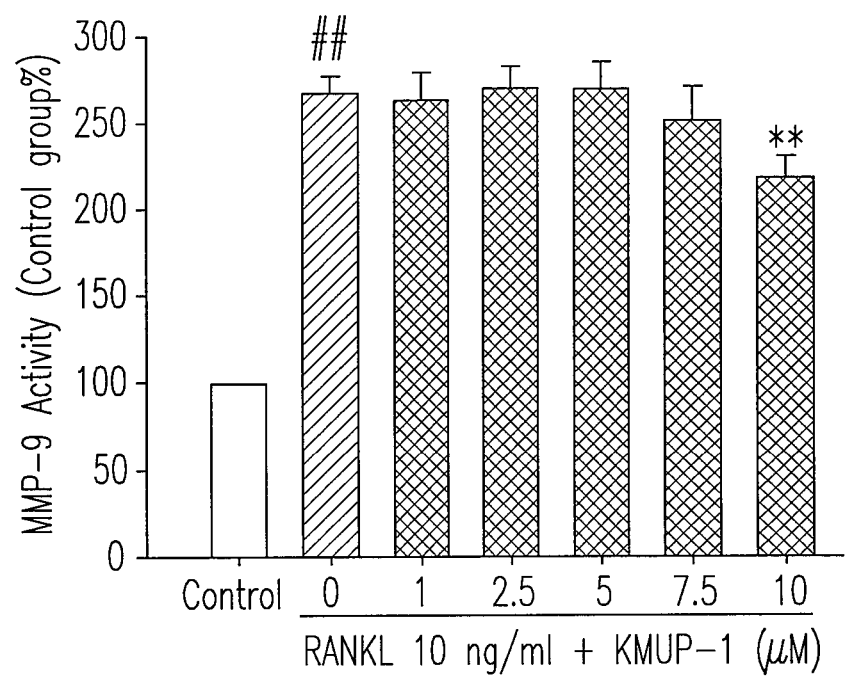
Figure 22A:
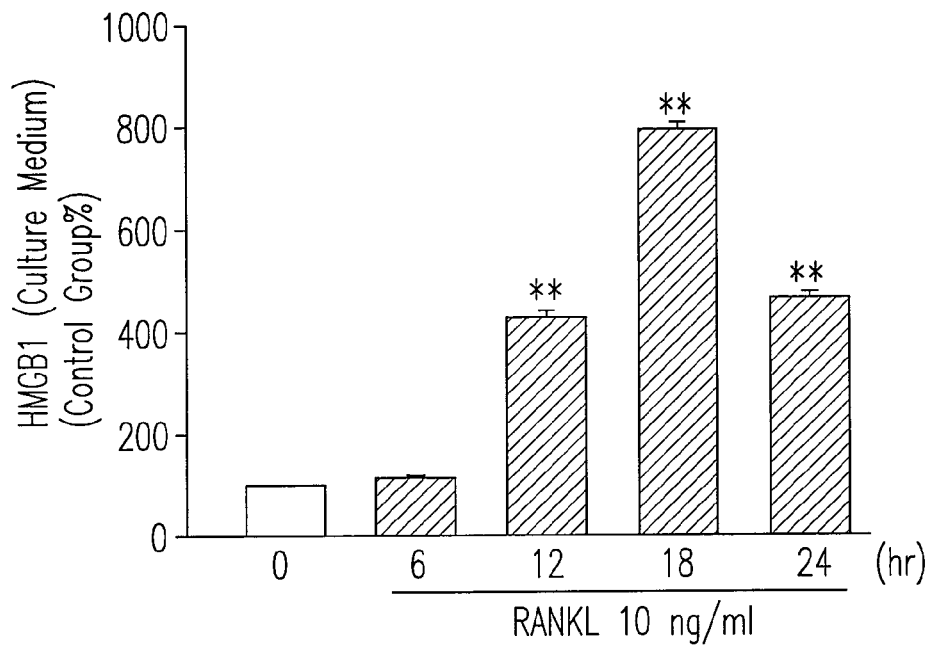
Figure 22B:
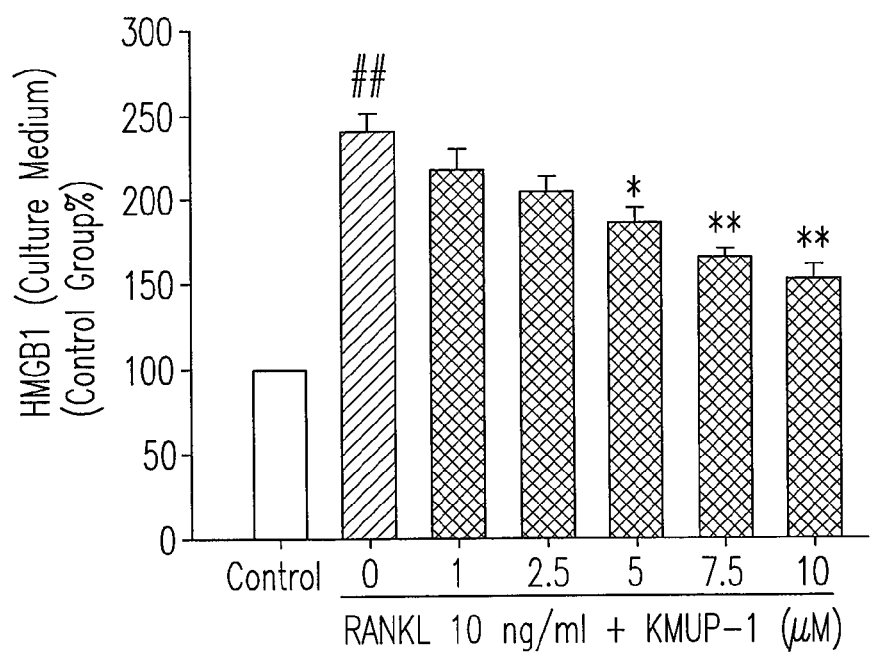
Figure 23A:
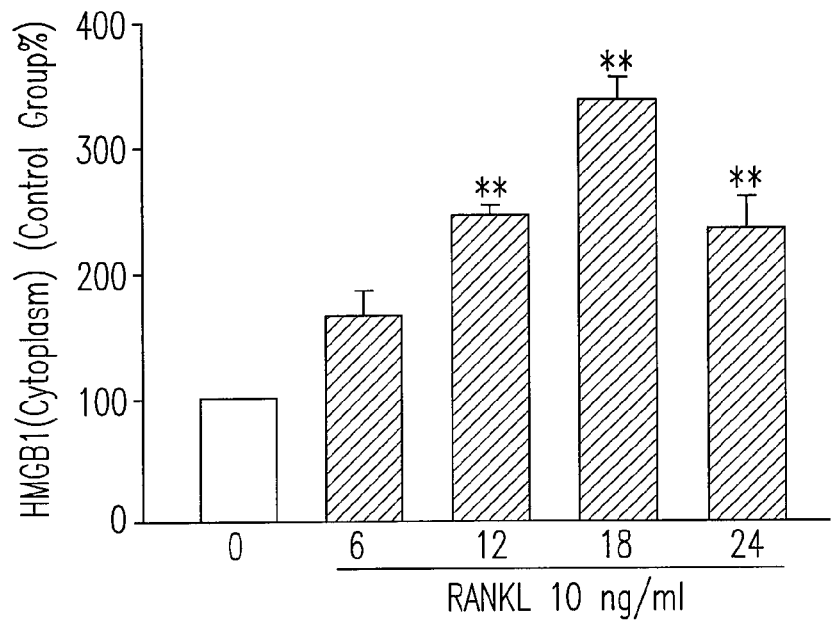
Figure 23B:
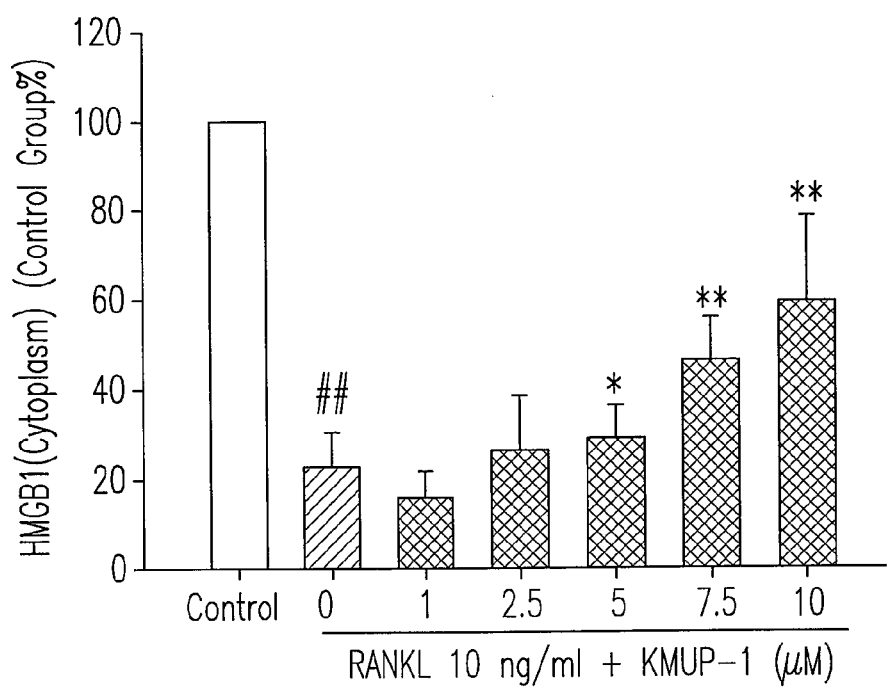
Figure 24A:
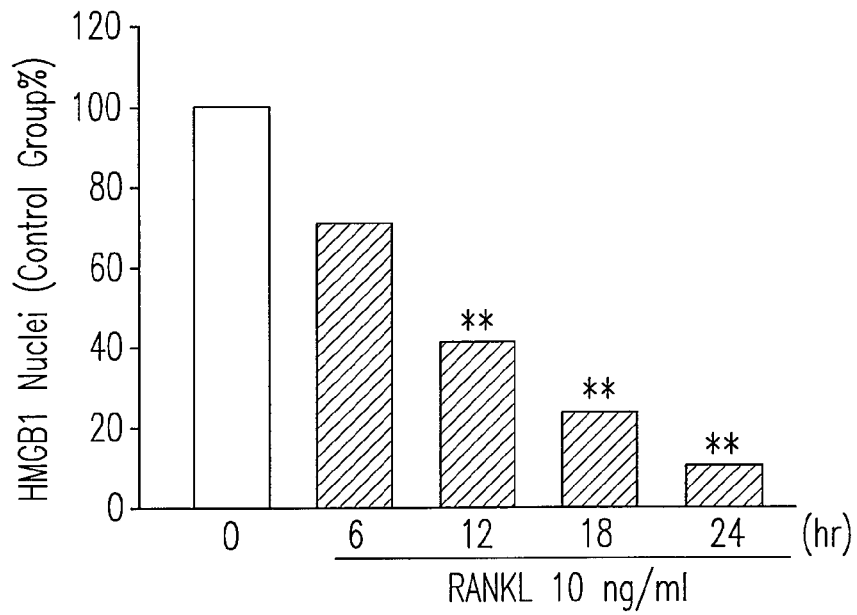
Figure 24B:
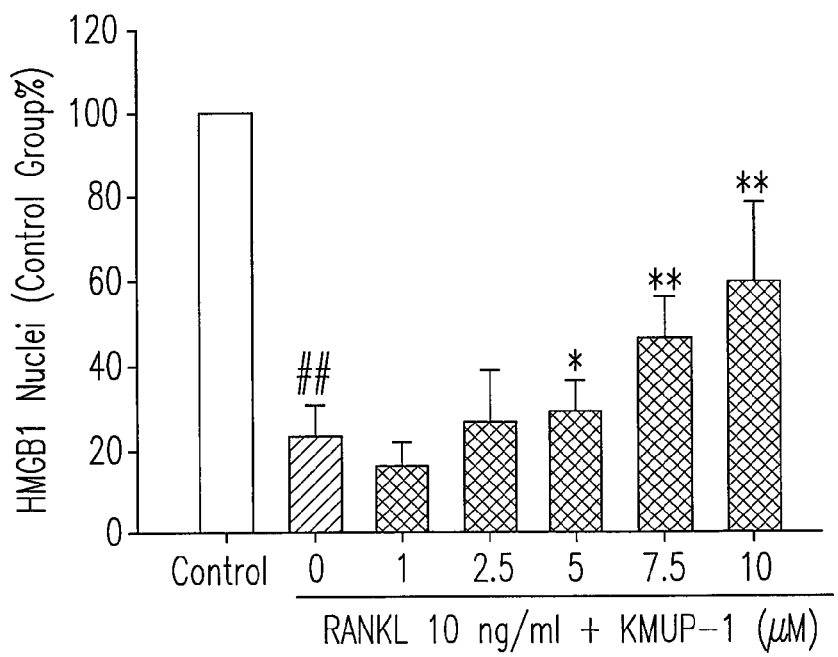
Figure 25:
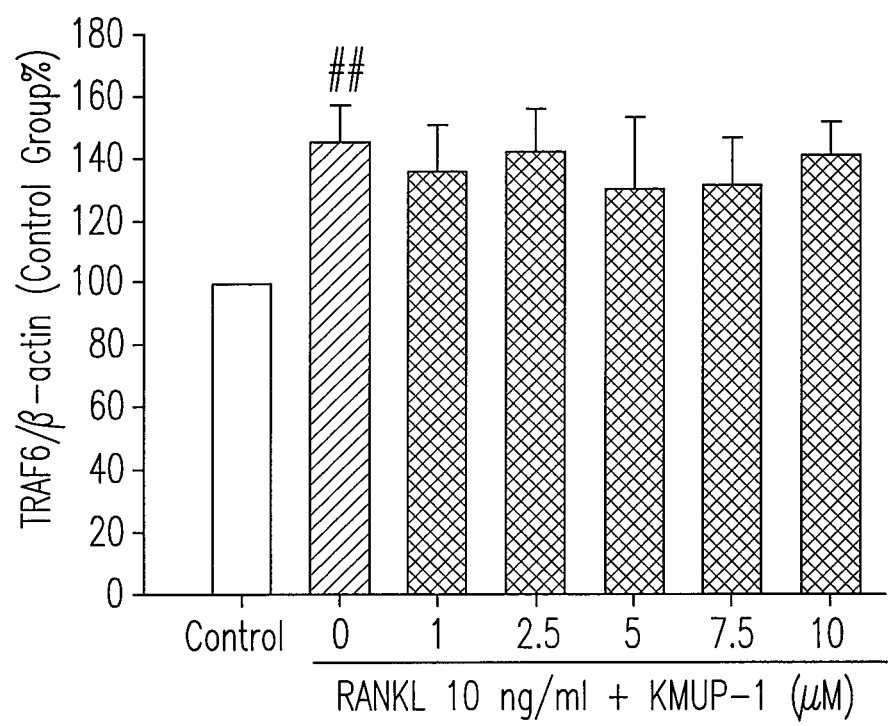

A) RANKL could not obviously stimulated the cellular calcium influx of RAW264.7 cells;
B) KMUP-1 inhibited that RANKL induced cellular calcium influx of osteoclast-like cells;
   ###$P<0.01$ compared with the control group;
   *$P<0.05$, **$P<0.01$ compared with the RANKL group FIG. 15 KMUP-1 inhibited that RANKL induced cellular calcium influx of osteoclast-like cells;
   ###$P<0.01$ compared with the control group;
   *$P<0.05$, **$P<0.01$ compared with the RANKL group FIG. 16 KMUP-1 inhibited the activation of calcineurin activated by RANKL;
   ###$P<0.01$ compared with the control group;
   **$P<0.01$ compared with the RANKL group FIG. 17 KMUP-1 inhibited the phosphorylation of Akt in cytoplasm;
   ###$P<0.01$ compared with the control group;
   *$P<0.05$, **$P<0.01$ compared with the RANKL group FIG. 18 KMUP-1 influenced RANKL to induce the production of MMP-2;
   ###$P<0.01$ compared with the control group;
   $P<0.05$, **$P<0.01$ compared with the RANKL group FIG. 19 KMUP-1 influenced RANKL to induce the production of MMP-9;
   ###$P<0.01$ compared with the control group;
   *$P<0.05$, **$P<0.01$ compared with the RANKL group FIG. 20 KMUP-1 influenced RANKL to induce the activity of MMP-2;
   ###$P<0.01$ compared with the control group;
   **$P<0.01$ compared with the RANKL group FIG. 21 KMUP-1 influenced RANKL to induce the activity of MMP-9;
   ###$P<0.01$ compared with the control group;
   **$P<0.01$ compared with the RANKL group FIG. 22 KMUP-1 influenced RANKL to stimulate the production of HMGB1 in the culture medium;
A) In each time period, 10 ng/ml RANKL induced the production of HMGB1
B) 10 ng/ml RANKL+KMUP ($\mu$M) induced the production of a day
   ###$P<0.01$ compared with the control group;
   *$P<0.05$, **$P<0.01$ compared with the RANKL group FIG. 23 KMUP-1 influenced RANKL to stimulate the production of HMGB1 in cytoplasm;
A) In each time period, 10 ng/ml RANKL induced the production of HMGB1
B) 10 ng/ml RANKL+KMUP ($\mu$M) induced the production of a day
   ###$P<0.01$ compared with the control group;
   *$P<0.05$, **$P<0.01$ compared with the RANKL group FIG. 24 KMUP-1 influenced RANKL to stimulate the production of HMGB1 in nuclei;
A) In each time period, 10 ng/ml RANKL induced the production of HMGB1
B) 10 ng/ml RANKL+KMUP ($\mu$M) induced the production of a day
   ###$P<0.01$ compared with the control group;
   *$P<0.05$, **$P<0.01$ compared with the RANKL group FIG. 25 KMUP-1 influenced the expression of TRAF6;
   ###$P<0.01$ compared with the control group

DETAILED DESCRIPTION OF THE PREFERRED EMBODIMENT

The present invention will now be described more specifically with reference to the following embodiments. It is to be noted that the following descriptions of preferred embodiments of this invention are presented herein for purposes of illustration and description only; it is not intended to be exhaustive or to be limited to the precise form disclosed.

Methods

Cell Culture:

Preparation of Culture Medium

10% FBS, 20 ml glutamine, 20 ml antibiotics, 3 g $NaHCO_3$ and DMEM powder were mixed together in 2000 ml $ddH_2O$ and was adjusted to pH 7.2.

Preparation of the First Generation of RAW264.7

After cells were defrosted, they were added in to 10 cm cell culture plates with suitable amount of the culture medium, an then were put in a incubator with 37° C., 5% $CO_2$/Air to wait for the attachment of the cells. On the next day, the culture medium was replaced to remove DMSO.

Preparation the Subculture of RAW264.7

After the old medium was removed, the cells were flushed down by the new culture medium and were counted by trypan blue and then were separated into other plates.

MTT Assay

Cells were plated onto 96-well plates at a density of $10^3$ cells per well. After 24 hours incubation, the different concentrations of the different drugs were administrated into the plates. At 24 hours and 48 hours, 10 $\mu$l/well MTT reagent (0.05 g/10 ml PBS) was added to the medium and the reaction was allowed to proceed for 4 hours. Subsequently, the medium was removed, and 100 $\mu$l/well isopropanol was added to solved formazan. The plates were shaken for 15 minutes and stood for 15 minutes, and then the absorbance was measured at wavelength of 540 nm and 630 nm. The ratio of the absorbance of treated cells relative to that of the control cells was calculated and expressed as a percentage of cell survival.

BrdU Assay

The BrdU assay was followed the instructions of Cell Proliferation ELISA BrdU kit. $10^3$ cells were plated per well in 96-well plates. After 24 hours incubation, the 10 ng/ml RANKL and the different concentrations of KMUP-1, theophylline and sildenafil were added into the plates. At 24 hours, 48 hours and 72 hours, 10 $\mu$l/well BrdU labeling reagent was added to the medium and the reaction was allowed to proceed for 4 hours in dark. Subsequently, the medium was removed, and 200 $\mu$l/well FixDenat solution was added and the reaction was allowed to proceed for 30 minutes at room temperature. Subsequently, the FixDenat solution was removed, and 100 $\mu$l/well Anti-BrdU POD was added and the reaction was allowed to proceed for 90 minutes at room temperature. After washing in wash buffer for three times, 100 $\mu$l/well Substrate reaction was added and incubated for 30 minutes at room temperature.

Antibodies or Staining Kit Against Tartrate Resistant Acid Phosphatase (TRAP Stain)

$10^3$ cells were plated per well in 96-well plates. After 24 hours incubation, the 10 ng/ml RANKL and the different concentrations of KMUP-1 were added into the plates, and the drug and the medium were renewed every 2 days, and the reaction was allowed to proceed for 4 days, and then the stain was conducted on the fifth day. After three washes in 37° C. PBS, 50 $\mu$l/well fluid was left. Subsequently, Fixative solution 200 $\mu$l/well was added into the plates, and the reaction was allowed to proceed for 10 minutes in room temperature, and then the plates were washed by $ddH_2O$ for three times. 50 $\mu$l/well fluid was left, and then Substrate 200 $\mu$l/well was added to react for 15 minutes in room temperature. After the cells were stained in red, the cells were washed by $ddH_2O$. At last, the cells were observed and taken pictures by an optical microscopy (40× and 200×), and Autopano Pro V1.4.2, Kolor, Paris, was used to proceed the pictures taken in 40×. Then, the number of the osteoclasts with at least three nuclei was counted and compared with the control group.

Recipe:
1. Fixative solution: Citrate solution 25 ml, Acetone 65 ml, 37% Formaldehyde 8 ml. Stored in dark in 4° C.
2. Citrate solution: 18 mM citric acid, 9 mM sodium citrate, and 12 mM NaCl were solved in 100 ml water, pH 3.6, and then 0.001% Triton X-100 was added at last.
3. Substrate: 2 mg AS-MX (Naphthol As-Mx-phosphate disodium) and 6 mg Fast Red Violet LB were solved in 1 M Sodium tartrate acetone (0.1 M, pH 5) and 0.1 M, 19 ml sodium acetate.

TRAP Activity Assay $10^3$ cells were plated per well in 96-well plates. After 24 hours incubation, the 10 ng/ml RANKL and the different concentrations of KMUP-1 were added into the plates, and the drug and the medium were renewed every 2 days, and the reaction was allowed to proceed for 4 days, and then the TRAP activity was examined on the fifth day. After three washes in ice-cold PBS, 50 µl/well Lysis buffer (with 0.2% TritonX-100) was added, and the reaction was allowed to proceed for 10 minutes. a) 5 µl/well supernatant was added to an other 96 well plate with 150 µl/well Substrate (0.1 M 4-NPP and 0.2 M Sodium tartrate in 0.1 M Sodium acetate, pH 5), and the reaction was allowed to proceed for 30 minutes in 37° C. in an incubator. When the reaction fluid became yellow, 0.1 M, 100 µl/well NaOH was added to terminate the reaction, and $OD_{405}$ was examined in 37° C. b) 3 µl/well supernatant was examined by Bio-Red DC Protein Assay to detect the protein concentration.

ELISA for Detecting TNF-α, IL-1β, IL-6, and IL-10

$10^5$ cells were plated per well in 24-well plates. After 24 hours incubation, the 10 ng/ml RANKL and the different concentrations of KMUP-1 were added into the plates. After 24 hours reaction, the reaction fluid was centrifuged (13,000 rpm, 4° C., 20 minutes), and then the supernatant was tasted by ELISA kit (R&D system and eBioscience™) to detect the amount of TNF-α, IL-1β, IL-6, and IL-10. The experimental process is followed with the instructions of the kit.

Nuclear-Cytosol Protein Separation a) Extraction of Cytoplasmic Proteins

Nuclear proteins were extracted according to the instructions of NE-PER kit. $2.5 \times 10^6$ cells were plated per well in 24-well plates. After 24 hours incubation, the different concentrations of KMUP-1 were added into the plates. After 24 hours reaction, the 10 ng/ml RANKL was added into the plates, and the cells were incubated for a specific time. After two washes in PBS, the cells were collected by scraping in 1 ml of ice-cold PBS and were put in centrifuge tubes. After centrifugation (5,000 rpm, 4° C., 5 minutes), the supernatant was discarded, and the cells were added by 100 µl CERI and were shaken for 15 seconds and then were put on ice for 10 minutes. Subsequently, the cells were added by 5.5 µl CERII and shaken for 5 seconds and then put on ice for 1 minute. After that, the cells were shaken again for 5 seconds and centrifuged (10,000 rpm, 4° C., 5 minutes). Cytoplasm and Nuclei could be separated by this process, and the supernatant was cytoplasmic proteins, and the pallet was nuclei. The supernatant was stored in an eppendorf in −80° C.

b) Extraction of Nuclear Proteins

The nuclear pallet was added by 500 µl PBS and centrifuged (10,000 rpm, 4° C., 5 minutes), and the supernatant was discarded. The pallet could be washed by this process and prevented contamination. The process that the pallet was added by 50 µl NER, shaken 15 seconds and put on ice for 10 minutes was repeated for four times. After centrifugation (13,000 rpm, 4° C., 10 minutes), the supernatant was nuclear proteins. The supernatant (nuclear proteins) was stored in an eppendorf in −80° C.

100% CERT:PI:PMSF=100:5:1   Formula of CER1:

100% NER:PI:PMSF=100:5:1   Formula of NER:

Western Blotting a) $10^6$ cells were plated in 6 cm culture dishes. After 24 hours incubation, the different concentrations of KMUP-1 were added into the plates. After 24 hours reaction, the 10 ng/ml RANKL was added into the culture dishes, and the cells were incubated for a specific time.

b) After two washes in ice-cold PBS and removing the PBS, the cells were added by 25 µl Lysis buffer, and the reaction was allowed to proceed for 10 minutes. The proteins were collected by scraping and were centrifuged (13,000 rpm, 4° C., 30 minutes). The supernatant was stored in an eppendorf in −80° C.

c) Concentrations of the proteins were examined by Bio-Red DC Protein Assay. After knowing the concentrations, the proteins were diluted to specific concentrations by adding $ddH_2O$. One forth volume of the diluted proteins of sample buffer was added into the diluted proteins and was put in boiled water for 5 min and then was chilled on ice for 5 minutes. After short time centrifugation, the diluted proteins could be injected into wells of a gel. The gel was run at 100 V for 10 minutes until the proteins were driven to the intersection between a loading gel and a running gel. Then, the voltage was swopped to 200 V for 40 minutes.

d) A PVDF membrane was immersed in Methanol for 2 minutes. After two washes in $ddH_2O$, the membrane was immersed in transfer buffer for 15 minutes. A SDS-PAGE was put on the membrane, and wet paper was flanked them. The proteins were transferred to the PVDF membrane using a semi-dry transfer at 20 V for 30 minutes.

e) The band of the PVDF membrane was trimmed and was added by suitable amount of blocking buffer (5% skim milk in washing buffer) and then was shaken for 1 hour in room temperature to block non specific bindings. Then, the band was covered by a diluted 1° antibody overnight in 4° C. After six washes in the washing buffer for 5 minutes, the band was covered by a 2° antibody for 1 hour in room temperature. After six washes in the washing buffer for 5 minutes, the band was probed by ECL.

Gelatin Zymography a) $2.5 \times 10^6$ cells were plated in 6 cm culture dishes. After 24 hours incubation, the 10 ng/ml RANKL and the different concentrations of KMUP-1 were added into the culture dishes. After 24 hours reaction, the reaction fluid was centrifuged (13,000 rpm, 4° C., 20 minutes), and then the supernatant was stored in −80° C.

b) 10% gel preparation. 10 mg gelatin was added by 1 ml $ddH_2O$ and then was heated in water bath until the solution was clear.

c) Concentrations of the proteins were examined by Bio-Red DC Protein Assay. After knowing the concentrations, the proteins were diluted to specific concentrations by adding $ddH_2O$. One forth volume of the diluted proteins of sample buffer was added into the diluted proteins. After shaking, the diluted proteins could be added into wells of the gel. Subsequently, 1× running buffer was added with the gel, and then the gel was run at 100 V for 10 minutes until the proteins were driven to the intersection between a loading gel and a running gel. Then, the voltage was swopped to 200 V for 60 minutes.

d) After electrophoresis, the loading gel was discarded, and the left gel was washed by TritonX-100 buffer for 30 minutes in room temperature twice. Subsequently, the left gel was washed by Tris-HCl buffer for 20 minutes in room temperature twice, Then, the left gel was added by Developing buffer in 37° C. water bath overnight.

e) After the Developing buffer was discarded, the stain and destain processes were conducted in a hood. The left gel was added by R-250 stain solution (Commassie blue) and was shaken gently for 40-60 minutes in room temperature. After the stain solution was retrieved, the left gel was added by destain solution and was shaken quickly. The destain solution was renewed every 5-10 minutes until a white band was appeared.

f) The washed gel was put on a transparent slid and was taken photo by a camera.

Pit Formation Assay

200 μl/well, 10 ng/ml RANKL and different the different concentrations of KMUP-1 were added into the 16-well slides of BD BioCoat™ Osteologic™ Bone Cell Culture System. Subsequently, 100 μl medium with 1,000 cells were added into each well, and the total volume was 300 μl/well. The slides were incubated for 5 days, and the medium and the drugs were renewed every 2 days. After 5 days, the medium was removed, and the cells were washed by $ddH_2O$ 3 times. Subsequently, the cells were covered by Bleach solution for staining 5 minutes and then were washed by $ddH_2O$ for 5 times. After drying, the cells were took a photo by an optical microscopy (40× and 200×), and Autopano Pro V1.4.2, Kolor, Paris, was used to proceed the pictures taken in 40×.

Reverse Transcription-Polymerase Chain Reaction, RT-PCR a) Cell Preparation $2.5 \times 10^6$ cells were plated in 6 cm culture dishes. After 24 hours incubation, the ng/ml RANKL and the different concentrations of KMUP-1 were added into the culture dishes, and the reaction was allowed to proceed for 24 hours.

b) Extraction RNA

The following processes were conducted in a laminar flow with nuclease-free tools. The culture medium was discarded. After 2-3 washes in ice-cold PBS, the cells were collected by scraping in 175 μl RNA lysis buffer (a new spatula was used for each plate). The scraped cell fluid was put in 1.5 ml eppendorfs and were added by 350 μl RNA Dilution Buffer and were mixed well. The eppendorfs were put in 70° C. water bath for 3 minutes (do not exceed 3 minutes), and were centrifuged (14,000 rpm, 4° C., 10 minutes). The supernatant was put in a new eppendorf.

c) Extraction RNA by a Spin Column

The supernatant was mixed with 200 μl, 95% Ethanol, and the fluid was transfer into a spin column. Then, the spin column was centrifuged (14,000 rpm, 4° C., 1 minute), and the fluid in a lower column was discarded. 50 μl DNase buffer was spread in a membrane of the spin column, and the reaction was allowed to proceed for 15 minutes. Subsequently, the spin column was added by 200 μl DNase stop solution and was centrifuged (14,000 rpm, 4° C., 1 minute). Then, 600 μl RNA wash solution was added into the spin column, and the spin column was centrifuged (14,000 rpm, 4° C., 1 minute). After that, 250 μl RNA wash solution was added into the spin column, and the spin column was centrifuged (14,000 rpm, 4° C., 2 minutes). The lower column was discarded, and the upper spin column was put in an eppendorf. 100 μl nuclease-free buffer was added into the spin column, and the spin column was centrifuged (14,000 rpm, 4° C., 1 minute). 2 μl dissolved RNA was conducted a concentration test, and the left RNA was stored in −80° C.

d) Reverse Transcription

After 1 μl RNA was put in a PCR machine for 10 minutes in 70° C., steam of the RNA sample was centrifuged down, and the RNA sample was chilled on ice. The RNA sample was added by solution A, and subsequently, the RNA sample with solution were put in the PCR machine (42° C. for 60 minutes, 95° C. for 5 minutes). After the reaction, cDNA concentration was examined and then added 80 μl water each tube. The RNA sample was stored in 4° C.

Preparation of solution A: 25 mM, 4 μl MgCl, 2 μl Reverse Transcription 10× Buffer, 10 mM, 2 μl dVTP Mixture, 0.5 μl Recombinant RNasin Ribonuclease Inhibitor, 0.6 μl AMV Reverse Transcription and 1 μl Oligo(dT) 15 primer OR Random Primers were mixed together, and at last 20 nuclease-free water was added into the above-mentioned mixture.

e) PCR Reaction

The following reagents were added in order. After the reagents were mixed well, the reagent mixture was put in the PCR machine to run the reaction.

| I. Taq Master Mix RED (2X) | 10 μl |
| II. Forword primer | 1 μl |
| III. Reverse primer | 1 μl |
| IV. Complementary DNA, cDNA | 2 μl |
| V. $ddH_2O$ | 6 μl | f) Running

A. Preparation of 2% agarose gel (1 peace): 1.2 g agarose was solved in 60 ml 0.5×TBE buffer by microwave (2-3 minutes, medium power) and was mixed with 1 μEtBr well. The mixture was poured into a modeling box.

B. preparation of a DNA ladder (Marker): DNA:loading dye:$ddH_2O$=1:2:7

C. Running buffer: 0.5×TBE buffer (about 300 ml)

D. Running at 100 V for 30-40 minutes g) Detection of an Intracellular Calcium Concentration A calcium ion fluorescent probe, fura-2/AM was used as an indicator for calcium concentration changes to detect the changes of the intracellular calcium concentration. The fura-2 could bind with calcium ions and was with fluorescent property. The wave length of the light activated by the fura-2 bound with calcium ions was 340 nm, but the wave length of the light activated by non binding fura-2 was 308 nm. According to this property, a ratio of the wave length intensity could be converted into the calcium concentration.

The macrophages of RAW264.7 rates were plated in 10 cm culture dishes. When the cells glowed to 90% saturated condition, $10^6$ cells were plated in 10 cm culture dishes. After 24 hours incubation, the 10 ng/ml RANKL was added into the culture dishes, and the reaction was allowed to proceed for 7 days. Until mono nuclear cells differentiated into multi-nuclear cells, culture medium was discarded. After 3-4 washes in PBS, the total cells were collected into eppendorfs by flushing with PBS, and then the eppendorfs were centrifuged (15,000 rpm, 4° C., 5 minutes). The supernatant was discarded, and the cells were added by 2 ml culture medium and 2.5 μl, 2 μM fura-2/AM, and the reaction was allowed to proceed for 40 minutes in 37° C., and then was centrifuged (15,000 rpm, RT, 5 minutes). The supernatant was discarded, and the cells were washed by suitable amount of physiological buffer and then were centrifuged. At last, the cells were added the suitable amount of physiological buffer to disarrange the cells. The concentration of the cells was adjusted to $5 \times 10^5$ cells/ml, and 1 ml cell suspension which was added KMUP-1 for 4 minutes in advance was put into a quartz tube. The quartz tube was put into a RF-5310 fluorescence spectrophotometer to detect changes of the 340 nm and 380 nm wave lengths which were activated by 510 nm wave length light. After recording for 60 seconds, 20 ng/ml RANKL was added into the cells, and the changes of intensity of light was detected.

Preparation of physiological buffer: 130 mM NaCl, 5 mM KCl, 10 mM Glucose, 1 mM MgCl, 1 mM CaCl and 29 mM HEPES were solved in 1 L ddH$_2$O and were adjusted to pH 7.4.

h) Monosodium Iodoacetate Animal Model

Monosodium iodoacetate (MIA) was used as an inducing agent for inducing osteoarthritis of rates. 30 five-week-old Wistar male rats (National Science Council of the R.O.C) with about 150-165 g weight were divided into five groups which are Sham, MIA induced group (MIA) and three KMUP-1 given groups (1, 2.5, 5 mg/kg KMUP-1), and each group was included 6 rates. After the rats were raised in an animal room for a week to adapt an environment, the rats were orally fed KMUP-1 (1, 2.5, 5 mg/kg) for a week. On the eighth day, the rats in the MIA group and the KMUP-1 given groups were injected 4 mg/25 µl, 0.5 ml MIA into left knee joints of the rats by a 26 mm insulin needle, and then the rats were fed KMUP (1, 2.5, 5 mg/kg) for a week. On the fifteenth day, when the rats were sacrificed, the left knee joints were opened, and a femur was separated from a tibia. The joint which was near the tibia of the femur was taken out. After cleaning, the joints were taken photos by a digital camera.

i) Tissue Sections

Ethylenediaminetetraacetic acid (EDTA) was added by ddH$_2$O and was heated until the EDTA was completely dissolved. A tissue from the joints was put into a tissue embedding cassette and was immersed in 10% formaldehyde for 3 days. Subsequently, the tissue was immersed in 0.5 M EDTA in 60° C. for a week in an oven to de-calcium. After the de-calcium bones were dehydrated for one day, the tissues were paraffin embedded and sliced which the slicing thick was 4 µm.

j) Stain

A. Hematoxylin & Eosin Stain, H&E

The sections were put in a 60° C. oven for 20 minutes and then were immersed in xylene for 3 minutes twice. Subsequently, the sections were immersed in 100% Ethanol for 3 minutes twice, 95% Ethanol 1 minute, 80% Ethanol for 1 minute, 80% Ethanol for 1 minute, 70% Ethanol for 1 minute, 50% Ethanol for 1 minute, ddH$_2$O for 1 minute and then Eosin for 1.5 minutes. After that, the sections were washed by flowing water for 5 minutes and were immersed in 90% Ethanol for 1-2 seconds, 100% Ethanol for 1-2 seconds and at last were immersed in xylene. At that time the sections could be sealed on a slide. The sealed slide was taken a photo under an optical microscopy.

B. Toluidine Blue

A preparation of Toluidine blue: 1% sodium borate, 1% Toluidine blue and 1% AZUR II were solved in ddH$_2$O.

C. The sections were put in a 60° C. oven for 20 minutes and then were immersed in xylene for 3 minutes twice. Subsequently, the sections were immersed in 100% Ethanol for 3 minutes twice, 95% Ethanol 1 minute, 80% Ethanol for 1 minute, 80% Ethanol for 1 minute, 70% Ethanol for 1 minute, 50% Ethanol for 1 minute, ddH$_2$O for 1 minute and then Toluidine blue for 1.5 minutes. After that, the sections were washed by flowing water for 5 minutes and were immersed in 90% Ethanol for 1-2 seconds, 100% Ethanol for 1-2 seconds and at last were immersed in xylene. At that time the sections could be sealed on a slide. The sealed slide was taken a photo under an optical microscopy.

k) Statistics

All experimental data were presented in Mean+S.E.M. and percentage (%). The comparisons of the experimental datum were presented by special marks and also were adopted Student's t-Test and one-way ANOVA to estimate differences between the control group and drugs given groups. When P value was less than 0.05, it expressed that there was an obvious difference in statistics.

REFERENCES

Armstrong A P, Tometsko M E, Glaccum M, Sutherland C L, Cosman D, Dougall W C: A RANK/TRAF6-dependent signal transduction pathway is essential for osteoclast cytoskeletal organization and resorptive function. J Biol Chem 2002, 277 (46):44347-44356.

Mizukami J, Takaesu G, Akatsuka H, Sakurai H, Ninomiya-Tsuji J, Matsumoto K, Sakurai N: Receptor activator of NF-kappaB ligand (RANKL) activates TAK1 mitogen-activated protein kinase kinase kinase through a signaling complex containing RANK, TAB2, and TRAF6. Mol Cell Biol 2002, 22 (4):992-1000.

Miyamoto K, Waki Y, Horita T, Kasugai S, Ohya K: Reduction of bone loss by denbufylline, an inhibitor of phosphodiesterase 4. Biochem Pharmacol 1997, 54 (5):613-617.

Takayanagi H: The role of NFAT in osteoclast formation. Ann N Y Acad Sci 2007, 1116:227-237.

Wei S, Siegal G P: Mechanisms modulating inflammatory osteolysis: a review with insights into therapeutic targets. Pathol Res Pract 2008, 204 (10):695-706.

Wong B R, Besser D, Kim N, Anon J R, Vologodskaia M, Hanafusa H, Choi Y: TRANCE, a TNF family member, activates Akt/PKB through a signaling complex involving TRAF6 and c-Src. Mol Cell 1999, 4 (6):1041-1049.

Yoshimura T, Kurita C, Nagao T, Usami E, Nakao T, Watanabe S, Kobayashi J, Yamazaki F, Tanaka H, Nagai H: Effects of cAMP-phosphodiesterase isozyme inhibitor on cytokine production by lipopolysaccharide-stimulated human peripheral blood mononuclear cells. Gen Pharmacol 1997, 29 (4):633-638.

Zhou Z, Han J Y, Xi C X, Xie J X, Feng X, Wang C Y, Mei L, Xiong W C: HMGB 1 regulates RANKL-induced osteoclastogenesis in a manner dependent on RAGE. J Bone Miner Res 2008, 23 (7):1084-1096.

What is claimed is:

1. A method of treating a bone disorder, comprising a step of administering to a subject in need thereof an effective amount of a pharmaceutical composition, wherein the pharmaceutical composition contains a pharmaceutically acceptable carrier and an effective amount of 7-[2-[4-(2-chlorophenyl)piperazin-1-yl]ethyl]theophylline, wherein the bone disorder is one selected from a group consisting of an osteoporosis, a knee cartilage injury, an osteoarthritis arthritis, a bone loss and a combination thereof.

2. The method as claimed in claim 1, wherein the pharmaceutically acceptable carrier is an excipient being one selected from a group consisting of solvents, dispersants, coatings, antibacterial agents, antifungal agents, saving absorbents, delaying absorbents and a combination thereof.

3. The method as claimed in claim 1, wherein the pharmaceutical composition is administered through one being selected from a group consisting of a vein, an oral, an inspiration, a nasal cavity, a rectum, a vagina, a hypoglossis and a combination thereof.

4. The method as claimed in claim 1, wherein the pharmaceutical composition is processed into one selected from a group consisting of a powder, a capsule, a tablet, a pill and a combination thereof.

5. The method as claimed in claim 1, wherein the pharmaceutical composition is administered to the subject in need with a dose from 0.1 g to 100 g per day.

* * * * *